(12) United States Patent
Lodish et al.

(10) Patent No.: US 7,405,193 B2
(45) Date of Patent: Jul. 29, 2008

(54) USE OF ACRP30 GLOBULAR HEAD TO PROMOTE INCREASES IN MUSCLE MASS AND MUSCLE DIFFERENTIATION

(75) Inventors: Harvey Lodish, Brookline, MA (US); Joachim Fruebis, Redmond, WA (US); Tsu-Shuen Tsao, Sommerville, MA (US); Bernard Bihain, Cancale (FR)

(73) Assignee: Serono Genetics Institute S.A., Evry (FR)

( * ) Notice: Subject to any disclaimer, the term of this patent is extended or adjusted under 35 U.S.C. 154(b) by 431 days.

(21) Appl. No.: 10/296,865

(22) PCT Filed: May 22, 2001

(86) PCT No.: PCT/IB01/01126

§ 371 (c)(1),
(2), (4) Date: Jul. 31, 2003

(87) PCT Pub. No.: WO01/92330

PCT Pub. Date: Dec. 6, 2001

(65) Prior Publication Data

US 2006/0035824 A1 Feb. 16, 2006

Related U.S. Application Data

(60) Provisional application No. 60/239,735, filed on Oct. 11, 2000, provisional application No. 60/208,251, filed on May 31, 2000.

(51) Int. Cl.
*A61K 38/00* (2006.01)
*A61K 38/22* (2006.01)

(52) U.S. Cl. .................. 514/2; 514/7; 514/8; 514/12
(58) Field of Classification Search .................. None
See application file for complete search history.

(56) References Cited

U.S. PATENT DOCUMENTS

| | | |
|---|---|---|
| 6,344,441 B1 | 2/2002 | Bihain et al. |
| 6,566,332 B2 | 5/2003 | Fruebis et al. |
| 6,579,852 B2 | 6/2003 | Fruebis et al. |
| 6,867,189 B2 | 3/2005 | Lucas et al. |
| 6,946,444 B2 | 9/2005 | Bihain et al. |
| 6,967,091 B2 | 11/2005 | Fruebis et al. |
| 6,989,367 B2 | 1/2006 | Fruebis et al. |
| 2002/0058617 A1 | 5/2002 | Fruebis et al. |
| 2004/0235709 A1 | 11/2004 | Salter-Cid et al. |
| 2005/0059631 A1 | 3/2005 | Fruebis et al. |
| 2005/0065079 A1 | 3/2005 | Scalia et al. |

FOREIGN PATENT DOCUMENTS

| | | |
|---|---|---|
| WO | WO 96/39429 A | 12/1996 |
| WO | WO 99/07736 A | 2/1999 |
| WO | WO 01/51645 A | 7/2001 |

OTHER PUBLICATIONS

Wells, 1990, Biochemistry 29:8509-8517.*
Ngo et al., 1994, The Protein Folding Problem and Tertiary Structure Prediction, pp. 492-495.*
Ouchi et al., Curr Opin Lipidol. 2003; 14: 561-6, see whole document.*
Masuzawa et al., Ann N Y Acad Sci. 1999; 892: 146-54.*
Ibánez and de Zeher, J Clin Endocrinol Metab. 2005; 90: 39-43.*
Fruebis et al., PNAS. 2001; 98:2005-2010.*
Yang et al. Biochem Biophys Res Commmun. 2006; 341: 209-217.*
Tan et al. Diabetologia. 2005; 48: 1585-1589.*
Satoh et al. Diabetes. 2005; 54: 1304-1313.*
Am. J. Physiol., Cell Physiol. 2006; 290: C650-9.*
Evans, WJ. Gerontology. 1998; 15: 15-24.*
Dehouck, M.-P., et al., "An Easier, Reproducible, and Mass-Production Method to Study the Blood-Brain Barrier In Vitro", *J. Neurochemistry* (1990), 54(5):1798-1801; Raven Press, Ltd., New York.
Shapiro, L. and Scherer, P. "The crystal structure of a complement-1q family protein suggests an evolutionary link to tumor necrosis factor", *Curr. Biol.* (1998), 8:335-338; Current Biology, Ltd.
Uysal, K.T., et al., "Protection from Obesity-Induced Resistance in Mice Lacking TNF-α Function", *Nature* (1997), 389:610-614; Macmillan Publishers Ltd.
Semsarian, C. et al. "Insulin-like growth factor (IGF-I) induces myotube hypertrophy associated with an increase in anaerobic glycolysis in a clonal skeletal-muscle cell model" *Biochem. J.*, 1999, pp. 443-451, vol. 339.
Galliano, M.-F. et al. "Binding of ADAM12, a Marker of Skeletal Muscle Regeneration, to the Muscle-specific Actin-binding Protein, α-Actinin-2, Is Required for Myoblast Fusion" *The Journal of Biological Chemistry*, May 5, 2000, pp. 13933-13939, vol. 275, No. 18.
Muscat, G. E.O. et al. "Not a minute to waste" *Nature Medicine*, Nov. 2000, pp. 1216-1217, vol. 6, No. 11.
Coleman, M.E. et al. "Myogenic Vector Expression of Insulin-like Growth Factor I Stimulates Muscle Cell Differentiation and Myofiber Hypertrophy in Transgenic Mice" *The Journal of Biological Chemistry*, May 19, 1995, pp. 12109-12116, vol. 270, No. 20.

* cited by examiner

*Primary Examiner*—Elizabeth C. Kemmerer
*Assistant Examiner*—Christina Borgeest
(74) *Attorney, Agent, or Firm*—Saliwanchik, Lloyd & Saliwanchik

(57) ABSTRACT

The present invention relates to the field of muscle research, in particular to the discovery of a compound effective for increasing muscle mass, muscle cell differentiation, and oxidation of free fatty acids in muscle, useful in methods of treating muscle-related diseases and disorders as well as for augmenting muscle mass in general. The muscle-related diseases or disorders envisaged to be treated by the methods of the invention include, but are not limited to, muscular dystrophy, and other conditions resulting in muscle atrophy or muscle wasting.

36 Claims, 6 Drawing Sheets

|  | 10 | 20 | 30 |  |
|---|---|---|---|---|
| 1 | M L L L G A V L L L | L A L P G H D Q E | - - - T T T Q G P G V | apm1protein |
| 1 | M L L L Q A L L F L | L I L P S H A E D D | V T T T E E L A P A | adipoQprotein |
| 1 | M L L L Q A L L F L | L I L P S H A E D D | V T T T E E L A P A | acrp30protein2 |

|  | 40 | 50 | 60 |  |
|---|---|---|---|---|
| 28 | L L P L P K G A C T | G W M A G I P G H P | G H N G A P G R D G | apm1protein |
| 31 | L V P P P K G T C A | G W M A G I P G H S | G H N G T P G R D G | adipoQprotein |
| 31 | L V P P P K G T C A | G W M A G I P G H P | G H N G T P G R D G | acrp30protein2 |

|  | 70 | 80 | 90 |  |
|---|---|---|---|---|
| 58 | R D G T P G E K G E | K G D P G L L G P K | G D I G E T G V P G | apm1protein |
| 61 | R D G T P G E K G E | K G D S G L L G P K | G E T G D V G M T G | adipoQprotein |
| 61 | R D G T P G E K G E | K G D A G L L G P K | G E T G D V G M T G | acrp30protein2 |

|  | 100 | 110 | 120 |  |
|---|---|---|---|---|
| 88 | A E G P R G F P G I | Q G R K G E P G E G | A Y V Y R S A F S V | apm1protein |
| 91 | A E G P R G F P G T | P G R K G E P G E A | A Y V Y R S G F S V | adipoQprotein |
| 91 | A E G P R G F P G T | P G R K G E P G E A | A Y M Y R S A F S V | acrp30protein2 |

|  | 130 | 140 | 150 |  |
|---|---|---|---|---|
| 118 | G L E T Y V T I P N | M P I R F T K I F Y | N Q Q N H Y D G S T | apm1protein |
| 121 | G L E T R V T V P N | V P I R F T K I F Y | N Q Q N H Y D N S T | adipoQprotein |
| 121 | G L E T R V T V P N | V P I R F T K I F Y | N Q Q N H Y D G S T | acrp30protein2 |

|  | 160 | 170 | 180 |  |
|---|---|---|---|---|
| 148 | G K F H C N I P G L | Y Y F A Y H I T V Y | M K D V K V S L F K | apm1protein |
| 151 | G K F Y C N I P G L | Y Y F S Y H I T V Y | M K D V K V S L F K | adipoQprotein |
| 151 | G K F Y C N I P G L | Y Y F S Y H I T V Y | M K D V K V S L F K | acrp30protein2 |

|  | 190 | 200 | 210 |  |
|---|---|---|---|---|
| 178 | K D K A M L F T Y D | Q Y Q E N N V D Q A | S G S V L L H L E V | apm1protein |
| 181 | K D K A V L F T Y D | Q Y Q E K N V D Q A | S G S V L L H L E V | adipoQprotein |
| 181 | K D K A V L F T Y D | Q Y Q E K N V D Q A | S G S V L L H L E V | acrp30protain2 |

|  | 220 | 230 | 240 |  |
|---|---|---|---|---|
| 208 | G D Q V W L Q V Y | G E G E R N G L Y A | D N D S T F T G F | apm1protein |
| 211 | G D Q V W L Q V Y | G D G D H N G L Y A | D N V D S T F T G F | adipoQprotein |
| 211 | G D Q V W L Q V Y | G D G D H N G L Y A | D N V D S T F T G F | acrp30protein2 |

| 238 | L L Y H D T N | apm1protein |
|---|---|---|
| 241 | L L F H D T - N | adipoQprotein |
| 241 | L L Y H D T - N | acrp30protein2 |

FIG. 1

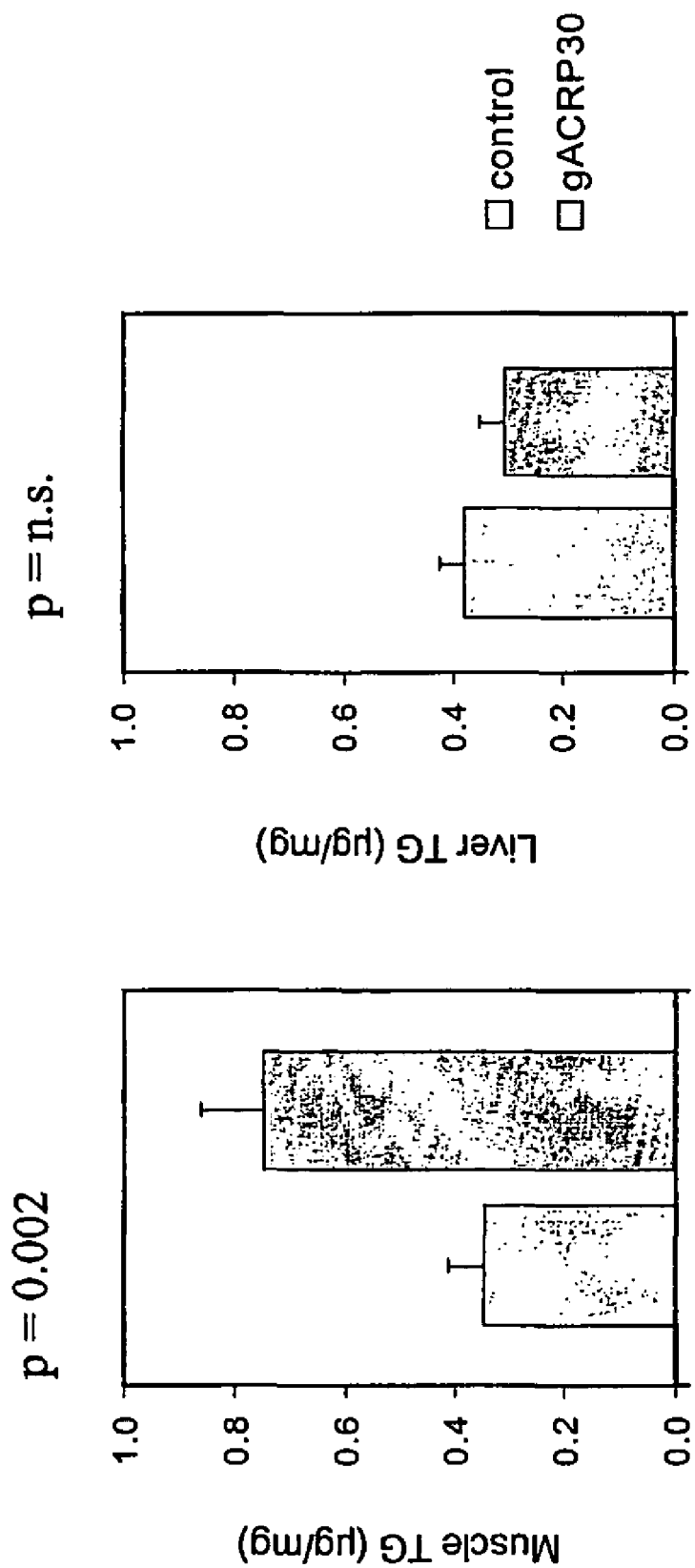

USE OF ACRP30 GLOBULAR HEAD TO PROMOTE INCREASES IN MUSCLE MASS AND MUSCLE DIFFERENTIATION

FIELD OF THE INVENTION

The present invention relates to the field of muscle research, in particular to the discovery of a compound effective for increasing muscle mass, muscle cell differentiation, and oxidation of free fatty acids in muscle, that should be useful in methods of treating muscle-related diseases and disorders as well as for augmenting muscle mass. The muscle-related diseases or disorders envisaged to be treated by the methods of the invention include, but are not limited to, muscle-related eye diseases and disorders, muscle-related recovery after injuries, muscle-related recovery after surgery, muscle-related disorders of aging, muscular dystrophy, and other conditions resulting in muscle atrophy.

BACKGROUND OF THE INVENTION

Acrp30 (also known as AdipoQ) is the murine homolog of the human Apm1 protein (this class of proteins is generically referred to as OBG3 herein). The predicted protein structure of Apm1 indicates the presence of: 1) a secreted protein signal peptide, 2) a region containing collagen repeats, and 3) a globular region (FIG. 2), which is highly conserved (FIG. 1).

Acrp30 is a circulating protein that is produced by the adipose tissue (WO 96/39429 which is hereby incorporated herein in its entirety including any figures, tables, or drawings). Acrp30 mRNA levels are significantly reduced in adipose tissue from obese ob/ob mice. Acrp30 expression is greatly increased during adipocyte differentiation and appears to be regulated by insulin. In addition, Acrp30 has been shown to reduce postprandial blood lipid levels, stimulate weight loss, and reduce plasma triglycerides in normal mice, and to promote the reduction of food intake in genetically obese mice (PCT Application No. 99/07736 which is hereby incorporated herein in its entirety including any figures, tables, or drawings).

Studies performed using just the globular region of Acrp30, termed globular Acrp30 (gAcrp30) showed that it effectively reduced body weight in mice on a high-fat cafeteria diet, as well as decreased fatty acid levels, decreased triglyceride levels, and improved glucose turnover in postprandial tests in mice (See U.S. Provisional Application Nos. 60/176,228 and 60/198,087, both of which are hereby incorporated herein by reference including any drawings, figures, or tables).

SUMMARY OF THE INVENTION

Globular OBG3 (gOBG3) has previously been linked with obesity, both in a murine model where treatment with gAcrp30 was shown to decrease body weight in mice fed a high fat diet, and in human subjects where an association between some Apm1 single nucleotide polymorphisms (SNPs) and obesity was documented. The instant invention is drawn inter alia to the unexpected effects of gOBG3 on muscle cells, including increasing the oxidation of free fatty acid in muscle cells as well as accelerating muscle re-orientation/re-organization and differentiation.

In a first aspect, the invention features methods of accelerating muscle cell differentiation, comprising contacting muscle cells with gOBG3 thereby accelerating differentiation of the muscle cells. Preferably the contacting is performed under conditions such that gOBG3 binds to the muscle cells. Preferably the muscle cells are present in an individual. Preferably, gOBG3 is present in a pharmaceutical composition. The pharmaceutical composition preferably further comprises a pharmaceutically acceptable diluent. gOBG3 can be provided as a polypeptide or as a polynucleotide encoding gOBG3. Preferably, gOBG3 is gApm1.

In a second aspect, the invention features methods of accelerating muscle cell reorganization, comprising contacting muscle cells with gOBG3 thereby accelerating reorganization of the muscle cells. Preferably the muscle cells are present in an individual. Preferably the contacting is under conditions such that gOBG3 binds to the muscle cells. Preferably, gOBG3 is present in a pharmaceutical composition. The pharmaceutical composition preferably further comprises a pharmaceutically acceptable diluent. gOBG3 can be provided as a polypeptide or as a polynucleotide encoding gOBG3. Preferably, gOBG3 is gApm1.

In a third aspect, the invention features methods of accelerating muscle repair, comprising contacting muscle cells with gOBG3 thereby accelerating reorganization and differentiation of the muscle cells. Preferably the contacting is under conditions such that gOBG3 binds to the muscle cells. Preferably the muscle cells are present in an individual. Preferably, gOBG3 is present in a pharmaceutical composition. The pharmaceutical composition preferably further comprises a pharmaceutically acceptable diluent. gOBG3 can be provided as a polypeptide or as a polynucleotide encoding gOBG3. Preferably, gOBG3 is gApm1.

In a fourth aspect, the invention features methods of increasing muscle mass in an individual, comprising contacting muscle cells in the individual with gOBG3 thereby accelerating the reorganization and differentiation of the muscle cells and increasing the muscle mass of the individual. Preferably said contacting is under conditions wherein gOBG3 binds to muscle cells. Preferably, gOBG3 is present in a pharmaceutical composition. The pharmaceutical composition preferably further comprises a pharmaceutically acceptable diluent. gOBG3 can be provided as a polypeptide or as a polynucleotide encoding gOBG3. Preferably, gOBG3 is gApm1.

In a fifth aspect, the invention features methods of treating muscle cell disorders in an individual, comprising contacting muscle cells in the individual with gOBG3 thereby accelerating the reorganization and differentiation of the muscle cells, and thereby treating the muscle cell disorders. Preferably the contacting is under conditions wherein gOBG3 binds to muscle cells. In preferred embodiments, the muscle cell disorders are selected from the group consisting of muscle-related eye diseases and disorders, muscle-related recovery after injuries, muscle-related recovery after surgery, muscle-related disorders of aging, muscle atrophy and muscular dystrophy. Preferably, gOBG3 is present in a pharmaceutical composition. The pharmaceutical composition preferably further comprises a pharmaceutically acceptable diluent. gOBG3 can be provided as a polypeptide or as a polynucleotide encoding gOBG3. Preferably, gOBG3 is gApm1.

Definitions

Before describing the invention in greater detail, the following definitions are set forth to illustrate and define the meaning and scope of the terms used to describe the invention herein.

As used herein, the term "OBG3" refers to any member of the family of homologous proteins that includes Apm1, the human homologue, as well as Acrp30 or AdipoQ, the mouse homologue. These proteins and the polynucleotides encoding them are described in detail in WO 96/39429 and U.S. patent application Ser. Nos. 60/176,228 and 60/198,087, all of which are hereby incorporated by reference herein in their entirety including any drawings, figures, or tables.

The term "polypeptide" refers to a polymer of amino acids without regard to the length of the polymer. Thus, peptides, oligopeptides, and proteins are included within the definition of polypeptide. This term also does not specify or exclude post-expression modifications of polypeptides. For example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferably a mammal. Both the terms "animal" and "mammal" expressly embrace human subjects unless preceded with the term "non-human".

The term "individual" as used herein refers to a mammal, including animals, preferably mice, rats, dogs, cattle, sheep, or primates, most preferably humans that perceives a need (or for whom a need is perceived) to accelerate muscle cell differentiation, to accelerate muscle cell reorganization, or to increase muscle mass. "Perceives a need" does not necessarily refer to a clinical need, but may simply be the result of an aesthetic desire to increase muscle mass, or to facilitate athletic training. An individual can also be a "patient".

The term "patient" as used herein refers to a mammal, including animals, preferably mice, rats, dogs, cattle, sheep, or primates, most preferably humans that are in need of treatment. The term "in need of treatment" as used herein refers to a judgment made by a medical care-provider such as a physician, nurse practitioner, nurse or the like, that a patient could benefit from or requires treatment. This judgement is made based on a variety of factors that are in the realm of the medical care-provider's expertise, but that include the knowledge that the patient is ill, or will be ill, as the result of a condition that is treatable by the compounds of the invention.

The term "accelerating muscle cell differentiation" as used herein refers to the ability of compounds of the invention to decrease the number of hours muscle cell differentiation requires in the absence of the compound (or alternatively stated, to increase the process of differentiation). This decrease in hours is at least 5 hours, preferably at least 10 hours, more preferably at least 20 hours. Alternatively, accelerating muscle cell differentiation can refer to the ability of compounds of the invention to increase the numbers of muscle cells undergoing differentiation at a given time, compared to the number in the absence of the compound, or to decrease the amount of apoptosis of muscle cells compared with the amount of apoptosis at a given time in the absence of the compound. Muscle cell differentiation can be determined by visual inspection (Example 1) or through markers of muscle cell differentiation known in the art, some of which are described in Shimokawa et al (1998) (Biochem Biophys Res Commun 246:287-292; hereby incorporated herein by reference in its entirety including drawings, figures, and tables; Example 6).

The term "accelerating muscle cell reorganization" as used herein refers to the ability of compounds of the invention to increase muscle cell reorganization in the presence of the compound as compared to in its absence. Alteratively, accelerating muscle cell reorganization can refer to the ability of compounds of the invention to increase the numbers of muscle cells undergoing reorganization at a given time, compared to the number in the absence of the compound. Muscle cell reorganization can be determined by visual inspection (Example 1).

The term "increasing muscle mass" as used herein refers to the ability of compounds of the invention to increase the number of differentiated muscle cells as compared to the numbers in the absence of the compound. Muscle cell differentiation can be determined by visual inspection (Example 1) or through markers of muscle cell differentiation known in the art, some of which are described in Shimokawa et al (1998). Increases in muscle mass can also be determined by measurements of the overall size of a muscle or the strength of a muscle using techniques well-known in the art.

The term "muscle cell disorders" as used herein refers to disorders where there is a loss of muscle mass, or muscle strength. These would include muscle atrophy or muscle wasting as the result of disease or trauma, or malnutrition, for example. In addition, disorders such as muscle-related eye diseases and disorders, muscle-related recovery after injuries, muscle-related recovery after surgery, muscle-related disorders of aging, and muscular dystrophy are specifically envisioned. Whereas some of these disorders would require a medical care provider's diagnosis (muscular dystrophy for example), others would simply require an individual to detect the change and desire the treatment (some forms of muscle wasting or muscle atrophy).

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-flame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/mL denatured salmon sperm DNA. Filters are hybridized for 48 h at 65° C., the preferred hybridization temperature, in prehybridization mixture containing 100 µg/mL denatured salmon sperm DNA and $5\text{-}20 \times 10^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency may also be used and are well known in the art (Sambrook et al., 1989 and Ausubel et al., 1989, both of which are hereby incorporated herein in their entirety including any drawings, figures, or tables). These hybridization conditions are suitable for a nucleic acid molecule of about 20 nucleotides in length. The hybridization conditions described can be adapted according to the length of the desired nucleic acid, following techniques well known to the one skilled in the art. The suitable hybridization conditions may, for example, be adapted according to Hames and Higgins (1985) or Sambrook et al. (1989).

BRIEF DESCRIPTION OF THE FIGURES

FIG. 1 shows an alignment of the sequences of the human (APM1), and mouse (adipoQ and acrp30) OBG3 proteins.

FIGS. 5A and 5B show graphical representations of the effect of gAcrp30 treatment on triglyceride content of muscle and liver isolated from mice. Mice that had received 25 µg of gAcrp30 twice daily showed significantly higher (p=0.002) muscle triglyceride content (FIG. 5A) than those receiving saline (control: light gray; gAcrp30: dark gray). This contrasted with a lack of increase in liver triglycerides (FIG. 5B).

FIG. 6A, Lane II shows the complete form of Acrp30 purified by FPLC. Lane I shows the proteolytic cleavage product gAcrp30. FIG. 6B shows a cleavage product of apm-1 after immunoprecipitation followed by Western blotting. The apparent molecular weight of this truncated form is 27 kDa, corresponding to about 70% of the complete form of apm-1 (Lane IV). This truncated form was not detectable when a second anti-serum, specific for the human non-homologous region (HDQETTTQGPGVLL-PLPKGA) of the protein was used for immunoprecipitation (Lane V) and the same anti-globular head antiserum for detection. A preimmune serum of the same animal did not detect any protein; a dimer of apm-1 was seen with both specific antibodies (apparent MW 74kDa).

DETAILED DESCRIPTION OF THE INVENTION

Figure 2:
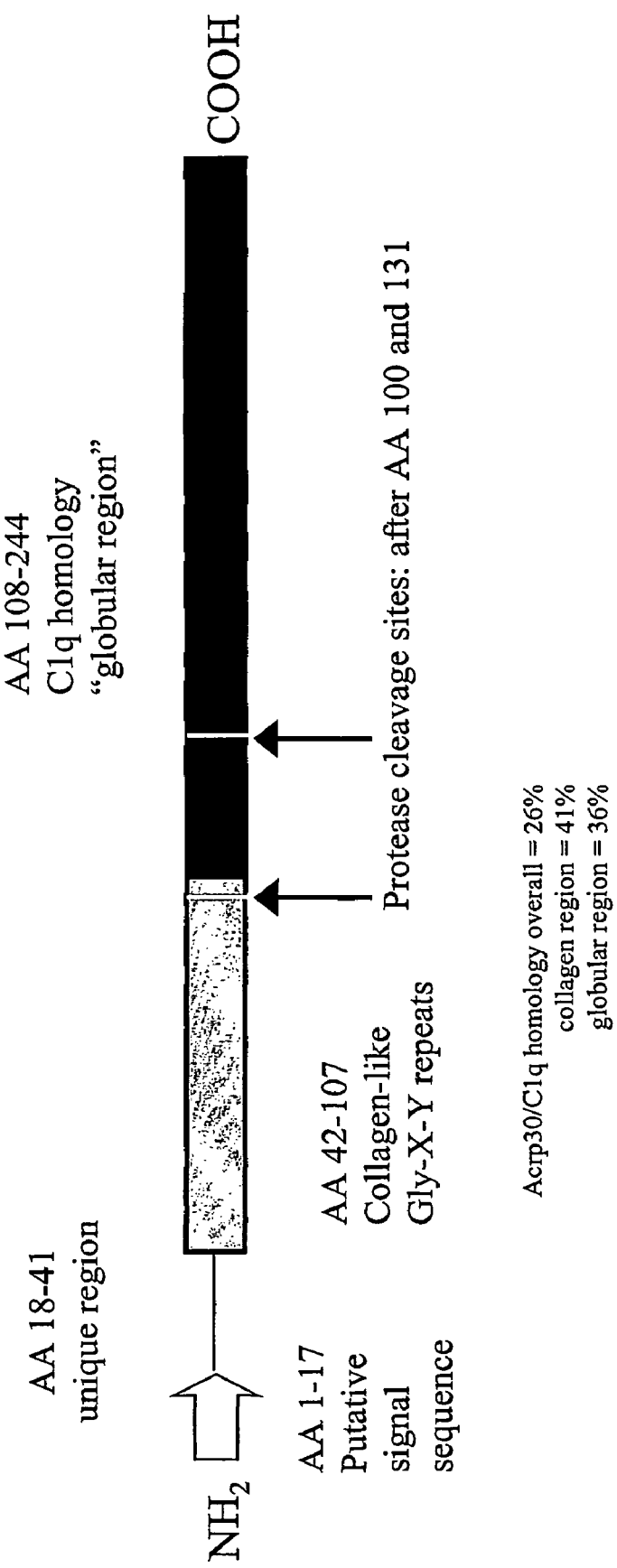
FIG. 2 shows a schematic drawing of the protein structure of APM1. The putative signal sequence at the N-terminus (AA 1-15), the unique region (AA 16-42), the collagen region (AA 43-107), and the globular region (AA 108-244) at the carboxy terminus are shown. Two protease cleavage sites at AA 100 and AA 131 are also shown.

Globular OBG3 has previously been linked with obesity, both in a murine model where treatment with globular Acrp30 (gAcrp30) was shown to decrease body weight in mice fed a high fat diet, and in human subjects where an association between some Apm1 single nucleotide polymorphisms (SNPs) and obesity was documented. In the instant application, the inventors have shown inter alia that at least some of the effects of gOBG3 are directed toward muscle cells. These effects include increasing the oxidation of free fatty acid in muscle cells as well as accelerating muscle re-organization and differentiation. Although the oxidation of free fatty acid in muscle cells likely is linked to the weight loss previously observed, it also seems to be linked to the acceleration of muscle cell reorganization and differentiation.

The effect of gAcrp30 on muscle cells was assessed using the murine, skeletal muscle cell line C2C12, and in ex vivo experiments on muscle cells excised from mice. The C2C12 cells were originally isolated from normal C3H mouse thigh muscle 72 hours after the muscle was crushed to increase the yield of mononucleated myogenic cells and designated C2 cells (Yaffe & Saxel (1977) Nature 270:725-727). The C2C12 cell line is a sub-clone of the C2 cell line selected for its ability to differentiate rapidly and to produce extensive contracting myotubes expressing characteristic muscle proteins (Blau et al (1985) Science 230:758-766). Thus, it appears that the C2C12 line is probably a clonal derivative of the satellite muscle cells present in muscle tissue that can replicate and differentiate to form additional muscle fibers.

Differentiation of C2C12 myocytes is induced when cultures are shifted to medium containing low concentrations of mitogens (Wang & Walsh (1996) Science 273:359-361). During this process myoblasts withdraw permanently from the cell cycle, express muscle specific structural proteins, and fuse into multinucleated myotubes (Davis et al (1987). Extensive cell death is also observed in cultures of C2C12 cells exposed to differentiation medium containing 2% horse serum beginning at 24 hours and reaching a maximum of 20-30% of cells at 48 hours (Wang & Walsh (1996)). After 72 to 96 hours myotubes become abundant and cell death is diminished.

The process of differentiation of the C2C12 cell line is a good model for studies for treatments of damaged muscle tissue following muscle injuries associated with strains and sprains, and tears normally encountered in daily life, as well as during intense athletic training, or as the result of accidental injury, or surgery. In all these instances, the muscle tissue is damaged, needs to re-orient/reorganize, and to grow new muscle fibers. Thus, treatments that enhance the reorientation/reorganization of the cultured muscle cells and their differentiation into muscle fibers should also be useful for accelerating the healing of muscle tissue following injury, as well as for accelerating the augmentation or strengthening of muscle cells during physical therapy, or athletic training.

Figure 3:
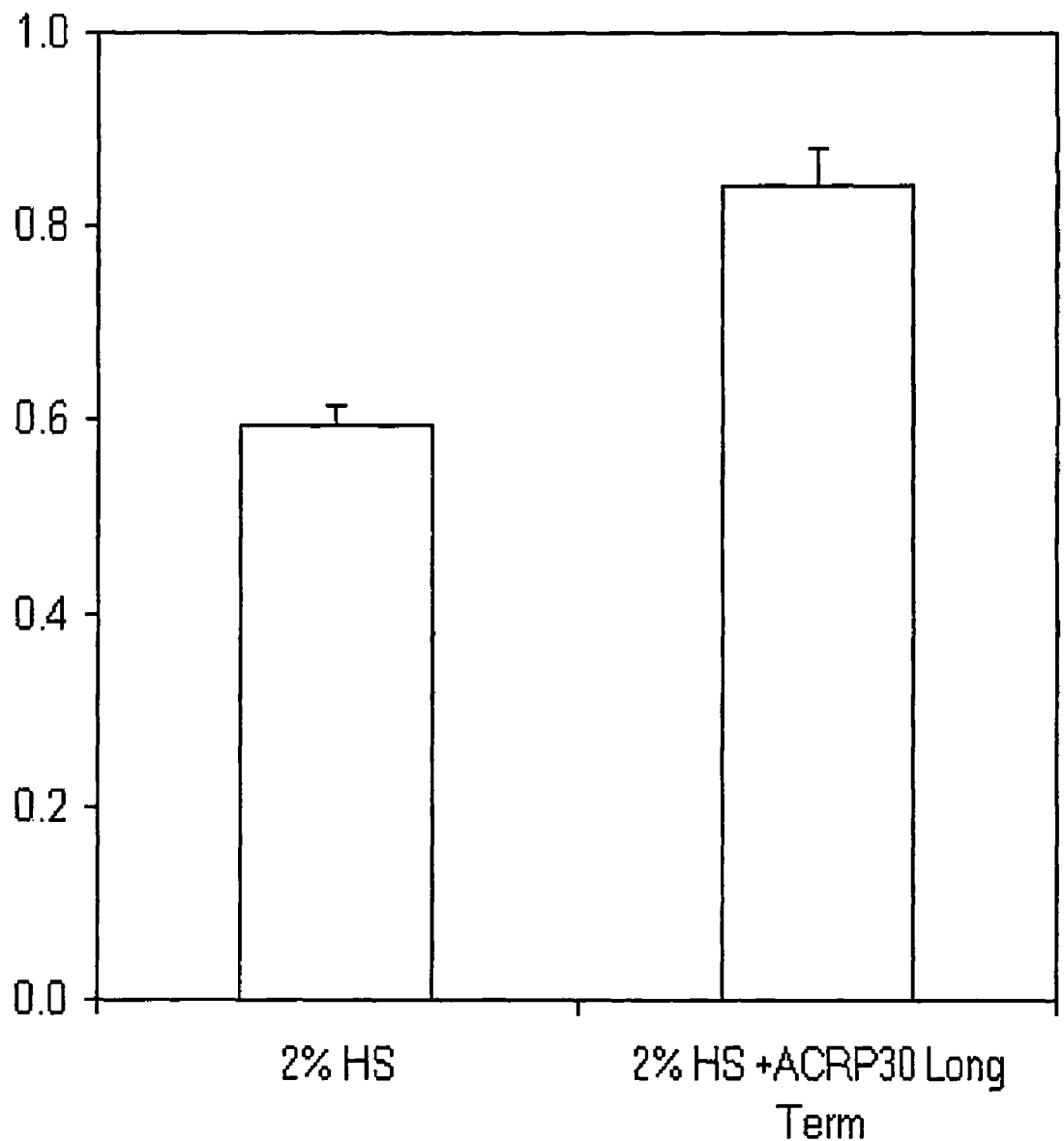
FIG. 3 shows a graphical representation of the effect of the addition of gACRP30 on the oleate oxidation of differentiated C2C12 cells.

Globular Acrp30 was found to induce pronounced re-orientation/re-organization of undifferentiated C2C12 muscle cells, as well as to accelerate the process of differentiation into muscle fibers. Further, there were indications of a decrease in apoptosis of muscle cells during the differentiation process, since the numbers of cells compared to the cells not treated with gOBG3 increased. Treatment of differentiated C2C12 cells with gAcrp30 also caused an increase in fatty acid metabolism, since oleate oxidation was increased approximately 40% (FIG. 3). A significant increase in oleate oxidation was also seen in ex vivo experiments with isolated mouse EDL and soleus muscles (FIG. 4), indicating the strength of the C2C12 cell line as a model system. A concurrent significant increase in triglyceride concentration was also observed in the ex vivo muscle.

Although not wishing to be limited to one hypothesis, the inventors believe that the increase in metabolism of free fatty acids that results from the addition of gAcrp30 may be involved in the acceleration of muscle cell reorientation/re-organization and differentiation. It is possible that the increase in fatty acid oxidation provides nutrients or energy that are involved in the process, or simply sends a signal. Whatever the exact mechanism involved, it is clear that treatment with gOBG3 has dramatic effects on muscle cells both in vitro and in vivo, for re-organization, differentiation and preventing apoptosis. Thus, it should be useful for treatment of muscle disorders where additional muscle tissue is desired and potentially where prevention of muscle cell death is needed. Examples of such disorders include, but are not limited to, muscle, wasting, muscle atrophy, or muscular dystrophy. Augmenting muscle differentiation and growth should be ameliorative to the symptoms, if not curative of the disease. Recruitment of more muscle cells, alignment, and differentiation of more muscle fibers should have a positive effect, and might at least prolong the useful life of the muscles of patients afflicted with muscular dystrophy.

PREFERRED EMBODIMENTS OF THE INVENTION

I. Muscle-Related Uses of gOBG3

Methods of Accelerating Muscle Repair:

The inventors have shown that treatment of muscle cells with gOBG3 leads to their re-organization and differentiation, as well as increased free fatty acid oxidation, processes believed to be important in muscle repair. The muscle cell line used is one created as the result of trauma to skeletal muscle cells and is therefore thought to be a good model for studying muscle repair. Treatments that accelerate muscle cell re-organization, muscle cell differentiation, and/or muscle cell repair would be useful following any kind of muscle injury, including, but not limited to trauma, either accidental, or the result of surgery, or over-exercising. Trauma to muscles can result from blows, tears, cuts, strains, etc. gOBG3 variants and fragments, as well as agonists and antagonists of gOBG3, can be tested for their activity and thus their potential for use as treatments for the acceleration of muscle repair using the assays described in the Examples (particularly Examples 1, 2, 4, 6, 7) or in other assays known to those in the art.

Methods of Increasing Muscle Mass:

In addition to muscle repair, the results of treatment of muscle cells with gOBG3 suggest that gOBG3 treatment could also be useful for increasing muscle mass and/or increasing muscle strength and/or muscle endurance. Increasing body mass (for aesthetic or sports-related reasons, for example) also involves the recruitment and development of new muscle cells, which gAcrp30 has been shown to promote in the experiments with C2C12 cells. Further, increased free fatty acid oxidation should also be useful in any kind of endurance or other activities leading to muscle fatigue, since free fatty acids are a better source of energy and generally less easily utilized than glucose stores. To some extent, gOBG3 would be expected to function similarly to the anabolic steroid-type drugs currently used by athletes. gOBG3 variants and fragments, as well as agonists and antagonists of gOBG3, can be tested for their activity and thus their potential for use for increasing muscle mass, strength and/or endurance using the assays described in the Examples (particularly Examples 1, 2, 4, 6, 7) or assays known to those in the art.

Methods of Treatment of Muscle Disorders:

For similar reasons as those that suggest gOBG3 would be useful for accelerating muscle repair and increasing muscle mass, and additionally because it appears that gOBG3 may be useful in preventing apoptosis, gOBG3 should also be useful for treating muscle cell disorders. The muscle cell disorders contemplated are those that would improve, or whose symptoms would be ameliorated by treatment with gOBG3. These would include disorders in which the cells need to be strengthened (improve utilisation of free fatty acid), or the amount of muscle fibers increased (increased differentiation of muscle cells). For example, gOBG3 would be expected to be useful for treating the muscle cell disorders muscle atrophy, muscle wasting, and muscular dystrophy. Treatment with gOBG3 is expected to ameliorate some symptoms of these diseases by increasing the strength of the existing muscle cells by increasing their use of free fatty acids, and by increasing the differentiation of additional muscle cells, as well as by preventing the apoptosis of existing muscle cells. For instance, even though in muscular dystrophy the existing muscles are abnormal and their use is gradually lost, it is thought that gOBG3 should be able to increase the useful life of the muscles. gOBG3 variants and fragments, as well as agonists and antagonists of gOBG3, can be tested for their activity and thus their potential for use as treatments for muscle disorders using the assays described in the Examples (particularly Examples 1, 2, 4-8) or in other assays known to those in the art.

II. Globular OBG3 Polypeptides

Globular OBG3 polypeptides are used in the methods of treating muscle cells of the instant invention. As used herein, the term "gOBG3" refers to the globular portion of any member of the family of homologous proteins that includes Apm1, the human homologue, as well as Acrp30 or AdipoQ, the mouse homologue. Globular OBG3 polypeptides have previously been described in detail in U.S. Provisional patent application Nos. 60/176,228 and 60/198,087, hereby incorporated by reference herein in their entirety including figures, drawings, or tables. As used herein, unless specifically limited, the term is meant to include modified gOBG3 polypeptide sequences, including variants, fragments, analogs and derivatives of the gOBG3 polypeptides as described previously.

For the purposes of this invention, however, useful gOBG3 polypeptides are those that retain any one or more of the desired activities described herein, including but not limited to the effects on muscle cells that are the subject of the instant invention. These include accelerating re-orientation and differentiation of muscle cells as well as increasing free fatty acid oxidation, and preventing apoptosis. Variants, fragments, analogs and derivatives of these polypeptide sequences can be assayed for their retention of the desired activities using any of the methods/tests described in Examples 1, 2, and 4-8 or any comparable assays.

Globular OBG3 is the portion of intact OBG3 that does not include the collagen-like tail, or that contains few enough of the collagen residues such that the peptides do not assemble, or if they assemble this does not inhibit their activity. Preferably, this is fewer than 6 collagen residues, fewer than 4, fewer than 2, or more preferably no collagen residues. By "collagen residues" as used herein is meant the amino acids glycine, X, Y, where X and Y can be any amino acid. The collagen-like region of OBG3 is shown in FIG. 2 for APM1.

The term "activity" as used herein refers to a measurable result of the interaction of molecules. For example, a preferred gOBG3 activity is to accelerate re-orientation of muscle cells, accelerate differentiation of muscle cells, and/or increase free fatty acid oxidation of muscle cells. Representative assays to test for these functions are provided in Examples 1, 2, and 4-9. However, these examples are provided for explanation, not limitation. Those with skill in the art would be able to design other experiments to test for the same retained activity.

The term the "same retained activity" as used herein refers to the ability of a variant, fragment, analog or derivative of gOBG3, to have the same activity as is demonstrated in Examples 1, 2, and 4-8 and claimed in the instant invention. The variant, fragment, analog or derivative of gOBG3 does not necessarily have to retain all of the activities described herein for gOBG3's action on muscle cells, unless specified, but preferably retains at least one of the activities.

The "same activity" also relates to the amount of a given activity observed. In the instant application this refers to the amount of oleate oxidation, or amount of acceleration of differentiation, or amount of prevention of apoptosis, for example. Preferably, the "same" activity as it relates to amount, means within 10% of the previously observed amount, but it can include a difference of 20% or 30% or even 50%. However, this is not meant to limit the use of more effective gOBG3 polypeptides.

"More effective" gOBG3 polypeptides include those with an increased activity compared with the gAcrp30 polypeptide used in experiments described herein. The term "increased" as used herein refers to the ability of gOBG3 polypeptides to increase an activity in some measurable way as compared to an appropriate control. As a result of the presence of a gOBG3 variant, the levels of fatty acid oxidation, or muscle cell differentiation might increase, or the amount of apoptosis might decrease, for example, as compared to appropriate controls, typically the presence of gAcrp30 used in the experiments described herein. Preferably, an increase in activity is at least 25%, more preferably at least 50%, most preferably at least 100%.

"More effective" gOBG3 polypeptides may also include those that lack or have a decreased amount of one activity compared with the gAcrp30 polypeptide used in experiments described herein, and an increased amount of another activity compared with the gAcrp30 polypeptide used in experiments described herein. The term "decreased" as used herein refers to the ability of gOBG3 polypeptides to decrease an activity in some measurable way as compared to an appropriate control, such as the gAcrp30 polypeptide used in experiments described herein. As a result of the presence of a gOBG3 variant, fatty acid oxidation might decrease, for example, as compared to controls in the presence of the gAcrp30 polypeptide used in experiments described herein. Preferably, a decrease in activity is at least 25%, more preferably at least 50%, most preferably at least 100%. The term "lack" as used herein refers to an inability to detect an activity using the methods described herein, or similar methods. A gOBG3 variant could be thought to "lack" activity even though an increase of 5 or 10 or 15% of an effect is observed compared with an assay performed in its absence.

Finally, "more effective" gOBG3 polypeptides may also include those that lack or have a decreased amount of one activity or all activities compared with the gAcrp30 polypeptide used in experiments described herein, but an increased amount of these activities in vivo as compared with the gAcrp30 polypeptide used in experiments described herein.

Preferred embodiments of the invention feature gOBG3 polypeptide that consists of the sequence of the globular region shown in FIG. 1, or variants, fragments, analogs, or derivatives thereof. Preferable embodiments include amino acids 108-244 of SEQ ID NO:6 or 111-247 of SEQ ID Nos. 2 and 4. Alternative preferable embodiments include amino acids 104 to 247 of the OBG3 proteins described in FIG. 1.

In other preferred embodiments, the invention features a gOBG3 polypeptide comprising at least 115, but not more than 175 contiguous amino acids of any one of the gOBG3 polypeptide sequences set forth in FIG. 1, wherein no more than 12 of said at least 115 and no more than 175 contiguous amino acids are present in the collagen-like region of OBG3. Preferably, the gOBG3 polypeptide comprises at least 125, but not more than 165, or at least 135, but not more than 155, and no more than 9 are in the collagen-like region; more preferably at least 125 but not more than 165, or 135 but not more than 155, and no more than 6 are in the collagen-like region; or at least 140 and not more than 150, and no more than 3 are present in the collagen-like region. Preferably the gOBG3 polypeptide is human or mouse, but most preferably human.

Variant gOBG3 polypeptides of the invention may be 1) ones in which one or more of the amino acid residues are substituted with a conserved or non-conserved amino acid residue and such substituted amino acid residue may or may not be one encoded by the genetic code, or 2) ones in which one or more of the amino acid residues includes a substituent group, or 3) ones in which a modified gOBG3 polypeptide is fused with another compound, such as a compound to increase the half-life of the polypeptide (for example, polyethylene glycol), or 4) ones in which the additional amino acids are fused to modify a gOBG3 polypeptide, such as a leader or secretory sequence or a sequence which is employed for purification of the modified gOBG3 polypeptide or a pre-protein sequence. Such variants are deemed to be within the scope of those skilled in the art. The retention of the desired activity (and thus desired gOBG3 polypeptides) can be determined using the assays described in Examples 1, 2, 4-8 or other assays that achieve the same result.

Amino acid changes present in a variant polypeptide may be non-conservative amino acid changes but more preferably are conservative amino acid changes. In cases where there are one or more amino acid changes, preferred gOBG3 polypeptides include those that retain the same activities and activity levels as the reference gOBG3 polypeptide sequence, as well as those where the level of one or more activities is increased. Assays for determining gOBG3 polypeptide activities of the invention are described herein in the Examples (1, 2, 4-8) in more detail, but include accelerating muscle differentiation, muscle oleate oxidation, and decreasing muscle apoptosis, both in vitro and in vivo.

In preferred embodiments, the invention features a variant of a gOBG3 polypeptide that is at least 75% identical to gOBG3 polypeptide sequences selected from the group consisting of 101-244, 108-244, and 132-244 of SEQ ID NO:6, or 104-247, 111-247, and 135-247 of SEQ ID Nos.2 or 4. Preferably, the amino acid sequence is at least 85% identical, more preferably 90% identical, most preferably 95% identical and optionally 100% identical. Preferably the sequence is human or mouse, and most preferably human.

In yet other preferred embodiments, the invention features a variant of a gOBG3 polypeptide that comprises (or consists of) a 143 contiguous amino acid sequence, wherein at least 100 of the 143 amino acids are identical to amino acids 101-244 of SEQ ID NO:6 or 104-247 of SEQ ID Nos. 2 or 4. Preferably, at least 113 of the 143 amino acids are identical, more preferably 127 of the 143 are identical, even more preferably 134 of the 143 are identical, and most preferably all of the amino acids are identical. Preferably the sequence is human or mouse, and most preferably human.

In yet other preferred embodiments, the invention features a variant of a gOBG3 polypeptide that comprises (or consists of) a 137 contiguous amino acid sequence, wherein at least 100 of the 137 amino acids are identical to amino acids 108-244 of SEQ ID NO:6 or 111-247 of SEQ ID Nos. 2 or 4. Preferably, at least 113 of the 137 amino acids are identical, more preferably 127 of the 137 are identical, even more preferably 134 of the 137 are identical, and most preferably all of the amino acids are identical. Preferably the sequence is human or mouse, and most preferably human.

In yet other preferred embodiments, the invention features a variant of a gOBG3 polypeptide that comprises (or consists of) a 113 contiguous amino acid sequence, wherein at least 80 of the 113 amino acids are identical to amino acids 132-244 of SEQ ID NO:6 or 135-247 of SEQ ID Nos. 2 or 4. Preferably, at least 90 of the 113 amino acids are identical, more preferably 100 of the 113 are identical, even more preferably 110 of the 113 are identical, and most preferably all of the amino acids are identical. Preferably the sequence is human or mouse, and most preferably human.

A polypeptide fragment is a polypeptide having a sequence that is entirely the same as part, but not all, of a given polypeptide sequence, preferably a gOBG3 polypeptide and variants thereof. Such fragments may be "free-standing", i.e. not part of or fused to other polypeptides, or they may be comprised within a single larger non-OBG3 polypeptide of which they form a part or region. However, several fragments may be comprised within a single larger polypeptide. As representative examples of gOBG3 polypeptide fragments of the invention, there may be mentioned those which have from about 5, 6, 7, 8, 9 or 10 to 15, 10 to 20, 15 to 40, 30 to 55, 40 to 70, 60 to 95, 80 to 130, or 90 to 144 amino acids long. Preferred are those fragments containing at least one amino acid substitution or deletion compared to a gOBG3 polypeptide.

III. Pharmaceutical Compositions

The gOBG3 polypeptides of the invention can be administered to a mammal, including a human patient, alone or in pharmaceutical compositions where they are mixed with suitable carriers or excipient(s). The pharmaceutical composition is then provided at a therapeutically or aesthetically effective dose. A therapeutically or aesthetically effective dose refers to that amount of gOBG3 sufficient to result in amelioration of symptoms of muscle-related disorders as determined by the methods described herein. A therapeutically or aesthetically effective dose can also refer to the amount of gOBG3 necessary for an increase in muscle mass or an increase in muscle strength or endurance in persons desiring this affect for aesthetic or athletic reasons alone. A therapeutically effective dosage of a gOBG3 polypeptide of the invention is that dosage that is adequate to promote muscle differentiation and/or increased free fatty acid oxidation, or decreased muscle cell apoptosis with continued or periodic use or administration. Techniques for formulation and administration of gOBG3 may be found in "Remington's Pharmaceutical Sciences," Mack Publishing Co., Easton, Pa., latest edition.

Other diseases or disorders that gOBG3 could be used to treat or prevent include, but are not limited to, muscle atrophy, muscle wasting and muscular dystrophy.

Routes of Administration

Suitable routes of administration include oral, rectal, transmucosal, or intestinal administration, parenteral delivery, including intramuscular, subcutaneous, intramedullary injections, as well as intrathecal, direct intraventricular, intravenous, intraperitoneal, intranasal or intraocular injections. A particularly useful method of administering compounds for promoting weight loss involves surgical implantation, for example into the abdominal cavity of the recipient, of a device for delivering gOBG3 over an extended period of time. Sustained release formulations of the invented medicaments particularly are contemplated.

Composition/Formulation

Pharmaceutical compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically acceptable carrier and at least one polypeptide that is a gOBG3 polypeptide of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical formulations for parenteral administration include aqueous solutions of the active compounds in water-soluble form. Aqueous suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to increase leptin or lipoprotein uptake or binding in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g. for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD5O and ED5O. Compounds that exhibit high therapeutic indices are preferred.

The data obtained from these cell culture assays and animal studies can be used in formulating a range of dosage for use in human. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to maintain the weight loss or prevention of weight gain effects. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10-90% of the time, preferably between 30-90%; and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

A preferred dosage range for the amount of a gOBG3 polypeptide of the invention, that can be administered on a daily or regular basis to achieve desired results, including a reduction in levels of circulating plasma triglyceride-rich lipoproteins, range from 0.01-50 mg/kg body mass. A more preferred dosage range is from 0.02-25 mg/kg. A still more preferred dosage range is from 0.1-20 mg/kg, while the most preferred range is from 0.2-10 mg/kg. Of course, these daily dosages can be delivered or administered in small amounts periodically during the course of a day.

EXAMPLES

Other characteristics and advantages of the invention are described in the Examples. The following Examples are provided for illustrative purposes and not as a means of limitation. One of ordinary skill in the art would be able to design equivalent assays and methods based on the disclosure herein, all of which form part of the instant invention.

Throughout this application, various publications, patents and published patent applications are cited. The disclosures of these publications, patents and published patent specifications referenced in this application are hereby incorporated by reference into the present disclosure.

Example 1

Effect of gACRP30 Treatment of Muscle Cells on Muscle Differentiation

C2C12 cells (murine skeletal muscle cell line; ATCC CRL 1772, Rockville, Md.) are seeded sparsely (about 15-20%) in complete DMEM (w/glutamine, pen/strep, etc)+10% FCS. Two days later they become 80-90% confluent. At this time, the media is changed to DMEM+2% horse serum to allow differentiation. The media is changed daily. Abundant myotube formation occurs after 3-4 days of being in 2% horse serum.

To test the effect of the presence of gACRP30 on muscle differentiation, gACRP30 (1 to 2 µg/mL) was added the day after seeding when the cells are still in DMEM w/10% FCS. Two days after plating the cells (one day after gACRP30 was first added), at about 80-90% confluency, the media was changed to DMEM+2% horse serum plus gACRP30.

The results show that the addition of gACRP30 causes the cells to begin organizing within one day after its addition. In contrast to the random orientation of the cells not treated with gACRP30, those treated with gARCP30 aligned themselves in relation to each other. In addition, differentiation progressed more rapidly in the presence o gAcrp30; after only 2 days of gACRP30 treatment maximal or near maximal differentiation was observed in contrast to the 3 to 4 days needed in its absence.

Example 2

Effect of gAcrp30 on Muscle Cell Fatty Acid Oxidation

C2C12 cells were differentiated in the presence or absence of 2 µg/mL gACRP30 for 4 days. On day 4, oleate oxidation rates were determined by measuring conversion of 1-$^{14}$C-oleate (0.2 mM) to $^{14}CO_2$ for 90 min. C2C12 cells differentiated in the presence of gACRP30 undergo 40% more oleate oxidation than controls differentiated in the absence of oleate (FIG. 3).

The effect of gAcrp30 on the rate of oleate oxidation was compared in differentiated C2C12 cells (murine skeletal muscle cells; ATCC, Manassas, Va. CRL-1772) and in a hepatocyte cell line (Hepa1-6; ATCC, Manassas, Va. CRL-1830). Cultured cells were maintained according to manufacturer's instructions.

The oleate oxidation assay was performed as previously described (Muoio et al (1999) Biochem J 338:783-791). Briefly, nearly confluent myocytes were kept in low serum differentiation media (DMEM, 2.5% Horse serum) for 4 days, at which time formation of myotubes became maximal. Hepatocytes were kept in the same DMEM medium supplemented with 10% FCS for 2 days. One hour prior to the experiment the media was removed and 1 mL of preincubation media (MEM, 2.5% Horse serum, 3 mM glucose, 4 mM Glutamine, 25 mM Hepes, 1% FFA free BSA, 0.25 mM Oleate, 5 µg/mL gentamycin) was added. At the start of the oxidation experiment, $^{14}$C-Oleic acid (1 µCi/mL, American Radiolabeled Chemical Inc., St. Louis, Mo.) was added and cells were incubated for 90 min at 37° C. in the absence/presence of 2.5 µg/mL gAcrp30. After the incubation period, 0.75 mL of the media was removed and was assayed for $^{14}$C-oxidation products as described for the muscle FFA oxidation experiment.

Oleate oxidation in C2C12 cells determined over 90 min increased significantly (39%; p=0.036, two-tailed t-Test) in cells treated with gAcrp30. In contrast, no detectable increase in the rate of FFA oxidation was seen in hepatocytes incubated with gAcrp30.

Triglyceride and Protein Analysis Following Oleate Oxidation in Cultured Cells Following the transfer of media for the oleate oxidation assay, cells were placed on ice. To determine triglyceride and protein content, cells were washed with 1 mL of 1×PBS to remove residual media. To each well, 300 µL of cell dissociation solution (Sigma) was added. Cells were incubated at 37° C. for 10 min. Plates were tapped to loosen cells, and 0.5 mL of 1×PBS was added. The cell suspension was transferred to an eppendorf tube, each well was rinsed with an additional 0.5 mL of 1×PBS, and the rinse was transferred to appropriate eppendorf tube. Samples were centrifuged at 1000 rpm for 10 minutes at room temperature. The supernatant was discarded, and 750 µL of 1×PBS/2% chaps was added to each cell pellet. The cell suspension was vortexed and was placed on ice for 1 hour. Samples were then centrifuged at 13000 rpm for 20 min at 4° C. Supernatants were transferred to new tubes and frozen at -20° C. until analyzed.

The amount of triglycerides in each sample was determined using Sigma Diagnostics GPO-TRINDER enzymatic kit. The procedure outlined in the manual was adhered to with the following exceptions: the assay was performed in a 48 well plate, 350 µL of sample volume was assayed, the control blank consisted of 350 µL PBS/2% chaps, and the standard contained 10 µL of the standard provided in the kit plus 690 µL PBS/2% chaps. Analysis of the samples was performed on a Packard Spectra Count at a wavelength of 550 nm.

Protein analysis was carried out on 25 µL of each supernatant sample using the BCA protein assay (Pierce) following manufacturer's instructions. Analysis of the samples was performed on a Packard Spectra Count at a wavelength of 550 nm.

Triglyceride production in both C2C12 and Hepa 1-6 cells did not change significantly in the absence/presence of Acrp30 and gAcrp30. The protein content of all cells analyzed was equivalent in the absence/presence of Acrp30 and gAcrp30.

Example 3

Production of Recombinant Acrp30

An illustrative method for producing recombinant OBG3 is given below. Although the method describes the production of the mouse analog, Acrp30, a person of ordinary skill in the art would be able to use the guidance provided to produce other OBG3 analogs, including but not limited to, the human analog, Apm1.

Recombinant Acrp30 is cloned in pTRC His B (Invitrogen) between BamHl and Xhol and maintained in *E. coli* DH5α. The sequence of the Acrp30 insert corresponds to Acrp 30 genbank U37222 bases 88 to 791, except in position 382 where in #3 G replaces A found in ACRP 30 (V instead of M). The corresponding nucleotide in AdipoQ U49915 is G as in clone #3. The amino acid V is also conserved in the human sequence Apm-1 D45371.

Culture:

Plate out bacteria in LB agar media containing 100 μg/mL ampicillin. Inoculate 1 colony into 5 mL media (no agar) at 37° C. overnight. Add 2 mL of this initial culture into 500 mL Erlenmeyer flasks containing 200 mL LB media and 100 μg/mL ampicillin. Incubate at 37° C. in an orbital shaker until the $OD_{600}$=0.2. Add IPTG to a final concentration of 1 mM (stock solution=1 M). Incubate at 37° C. overnight.

Lysis:

Pellet the bacteria by centrifugation (Sorvall, 3500 rpm, 15 min, 4° C.) in a pre-weighed tube.

At 4° C. resuspend the pellet in 3 mL/g of lysis buffer
Add 40 μg PMSF 10 mM
Add 80 μL/g of lysozyme 1.0 mg/mL
Incubate 20 min on ice, shaking intermittently
Add 30 μL/g 10% sodium deoxycholate
Incubate at 37° C., until the lysate is viscous
Freeze in liquid Nitrogen and thaw at 37° C. three times
Sonicate 2×, 30 sec, 25% cycle, 2.5 power level
Centrifuge 30 min, 15000 rpm, 4° C.
Recover the supernatant
Note: The lysate can be stored frozen before or after the sonication step.

Batch Purification:

1. Pack 1 mL of Probond resin (Invitrogen, 1 mL=2 mL suspended gel) into a 5 mL column. Wash with 5 mL PBS.
2. Apply 5 mL bacterial supernatant to the 1 mL of gel. (If volume is very high, use several small columns.)
3. Wash with 24 mL phosphate buffer, pH 7.8, followed by a wash with 24 mL phosphate buffer, pH 6.
4. Elute with imidazole buffer and collect fractions of 1 mL.
5. Analyze fractions by OD at 280 nm or by SDS-PAGE (12.5%; dilution ½ in 2× sample buffer) under reducing conditions (100° C., 5 min)
6. Pool the fractions containing protein (usually fraction numbers 2-4 for concentrations of 08-1 mg/mL and fractions 1, 5 and 6 for concentrations of 0.2-0.4 mg/mL).
7. Dialyze thoroughly against 1×PBS, 24 mM ammonium bicarbonate or 50 mM Tris, pH 7.4 containing 250 nM NaCl. Concentrate by Speed-Vac if needed.
8. Analyze protein by the Lowry method.
9. Aliquot and store at −20° C.

Purification on Liquid Chromatography System

1. Pack 5 mL of Probond resin into a 5 mL column.
2. Wash with 4 bed volumes of phosphate buffer pH 7.8, 1 mL/min.
3. Inject 25 mL lysate (filtered on 0.45μ or centrifuged at 3000 rpm, 30 min, 4° C., Beckman Allegra 6R) at 0.5 mL/min.
4. Wash with 4 bed volumes of phosphate buffer, pH 7.8 at 1 mL/min.
5. Wash with 12 bed volumes of phosphate buffer pH 5.5 at 1 mL/min.
6. Elute bound fraction with phosphate buffer, pH 5.5, containing 1 M imidazole at 1 mL/min.
7. Collect fractions, dialyze and analyze protein as described for batch purification, steps 7-9.

Example 4

Generation of Globular Acrp30 by Enzymatic Cleavage

Incubate purified Acrp30 (obtained as described above or through equivalent method) with acetylated Trypsin-Type V-S from Bovine Pancreas (Sigma E.C.=3.4.21.4) at 400 u/mg protein at 25° C. for 10 min.

Stop reaction by running the sample over a Poly-Prep Column (Biorad 731-1550) at +4° C. containing immobilized Trypsin inhibitor.

Collect 1.0 mL fractions. Determine protein concentration.
Pool the protein containing fractions and dialyze extensively against PBS using dialysis tubing with M.W. cut-off=10,000 da.

Concentrate on Amicon YM-10 Centricon Filter (Millipore, M.W. cutoff=10,000 da). Sterile filter.

Determine final protein concentration using Markwell's modified Lowry procedure (1981) or BCA protein assay (Pierce Chemical Co, Rockford, Ill.) and BSA as standard.

Check purity and efficiency of cleavage by SDS-PAGE analysis using a 4-20% gradient gel. The intact Acrp30 migrates as a single band at approx. 37 kda due to co-transcribed vector sequences attached to the histidine tag at the N-terminus of Acrp30. The cleaved Acrp30 forms a band at approx. 18 kda (gAcrp30). Additional degradation products, all smaller than 10 kda are also generated from the N-terminal region. These are separated from the desired 18 kda band by dialysis with semipermeable membranes with a MW cutoff of 10,000. The actual cleavage site using this method has been identified as the one after amino acid 103.

Example 4

Effect of ACRP30 on Oleate Oxidation in Isolated Muscle

Intact muscles were isolated from C57BL6/J mice and the oleate oxidation of the isolated muscle was measured (Clee et al (2000) J Lipid Res 41:521-5351; Muoio et al (1999) Am J Physiol 276:E913-921). Oleate oxidation in isolated muscle was measured as previously described (Cuendet et al (1976) J Clin Invest 58:1078-1088; Le Marchand-Brustel (1978) Am J Physiol 234:E348-E358, hereby incorporated by reference herein in its entirety including any figures, drawings, or tables).

Two groups of C57BL6/J mice, age 5 and 33 weeks, were used. Mice were kept on a regular diet with free access to food and water. The day/night light cycle was kept at 12 hr ON/12 hr OFF. The older animals were injected twice daily with either saline or 25 μg of gACRP30 for 3-4 days. The younger group of animals was given a high fat meal (6 g butter, 6 g sunflower oil, 10 g nonfat dry milk, 10 g sucrose, 12 mL distilled water prepared fresh) by gavage (vol.=1% of body weight) at time 0 and was injected with saline or gACRP30 only at time 0 and again at 45 minutes. They were sacrificed at 180 minutes. The gACRP30 used was prepared as described in Example 3.

After cervical dislocation, soleus and EDL muscles were rapidly isolated from the hind limbs of the mice. The distal tendon of each muscle was tied to a piece of suture to facilitate transfer among different media. All incubations were carried out at 30° C. in 1.5 mL of Krebs-Ringer bicarbonate buffer (118.6 mM NaCl, 4.76 mM KCl, 1.19 mM $KH_2PO_4$, 1.19 mM $MgSO_4$, 2.54 mM $CaCl_2$, 10 mM Hepes, pH 7.4) supplemented with 4% bovine serum albumin, FFA free (fraction V, RIA grade, Sigma, Inc., St. Louis, Mo.) and 5 mM glucose (Sigma, Inc., St. Louis, Mo.). The concentration of oleate (Sigma, Inc., St. Louis, Mo.) throughout the experiment was 0.25 mM. All media were oxygenated (95% $O_2$; 5% $CO_2$) prior to incubation. The gas mixture was hydrated throughout the experiment by bubbling through a gas washer (Kontes Inc., Vineland, N.J.).

Muscles were rinsed for 30 min in incubation media with oxygenation. The muscles were then transferred to fresh media (1.5 mL) and incubated at 30° C. in the presence of 1 µCi/mL [1-$^{14}$C]oleic acid (ARC) and 1 µCi/mL [5-$^3$H]-glucose (Amersham). The incubation vials containing this media were sealed with a rubber septum from which a center well carrying a piece of Whatman paper (1.5 cm×11.5 cm) was suspended.

After an initial incubation period of 10 min with constant oxygenation, gas circulation was removed to close the system to the outside environment. The muscles were incubated for an additional 90 min at 30° C. At the end of this period, 0.45 mL of Solvable (Packard Instruments, Meriden, Conn.) was injected onto the Whatman paper in the center well. The oxidation of oleate by the muscle was stopped at this time point by transferring the vial onto ice.

After 5 min, the muscle was removed from the medium, was cleaned of connective tissue, was weighed and was frozen for further analysis. An aliquot of 0.5 mL medium was removed, the vials were closed again and 1 mL of 35% perchloric acid was injected with a syringe into the media by piercing through the rubber septum with a needle. The $CO_2$ released from the acidified media was collected by the Solvable in the center well.

After a 90 min collection period at 30° C., the Whatman paper was removed from the center well and placed in scintillation vials containing 15 mL of scintillation fluid (HionicFlour, Packard Instruments, Meriden, Conn.). The amount of $^{14}$C radioactivity was quantitated by liquid scintillation counting. The rate of oleate oxidation was expressed as nmol oleate produced in 90 min/g muscle.

Figure 4:
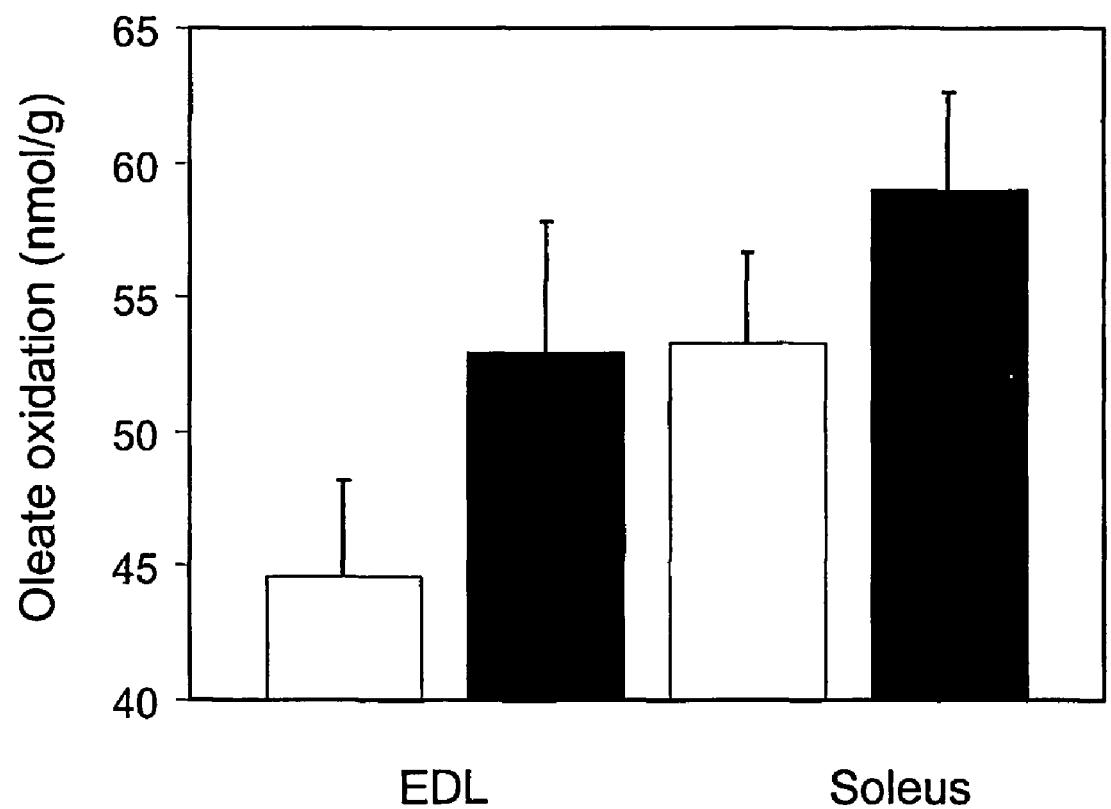
FIG. 4 shows a graphical representation of the effect of gAcrp30 treatment on fatty acid metabolism in muscle isolated from mice. EDL and Soleus muscles were isolated from both legs of each mouse (n=18). One muscle of each pair was incubated in medium with 2.5 µg/mL gAcrp30 (dark gray) and one in medium without gAcrp30 (control-light gray).

To test the effect of gACRP30 or ACRP30 on oleate oxidation, these proteins were added to the media at a final concentration of 2.5 µg/mL and maintained in the media throughout the procedure. Two muscles of different oxidative capacity (soleus and extensor digitorum longus (EDL)) were tested (FIG. 4). EDL and Soleus muscles were isolated from both legs of normal C57BL/6J mice (n=18). One muscle of each pair was incubated in medium with 2.5 µg/mL gAcrp30 (dark gray) and one in medium without gAcrp30 (control-light gray). This experimental design allowed us to compare oleate oxidation in pairs of muscles isolated from the same animal. $^{14}$C-Oleate oxidation was determined over 90 minutes. Incubation of EDL and soleus muscles for 90 minutes in medium containing 2.5 µg/ml gAcrp30 leads to a statistically significant increase in oleate oxidation (p<0.05, paired, one-tailed, t-Test) or (p=0.0041, Repeated Measures Analysis of Variance, Univariate Tests of Hypotheses for Within Subject Effects) in both muscle types.

Both muscle types showed a significant response to gAcrp30. The relative increase in FFA oxidation was 17% (p=0.03) and 10% (p=0.04) for EDL and soleus, respectively. In humans, muscles represent approximately 25% of body weight. Therefore, even a moderate increase in free fatty acid oxidation can have quantitatively important consequences on overall energy utilization.

In summary, these experiments show that gAcrp30 acts on muscle cells in vivo and ex vivo. The invention is drawn, inter alia, to the effects of gAcrp30 on muscle resulting in increased lean muscle mass and exercise capability. The increase in oleate oxidation seen in these whole muscle experiments, suggests that experiments done using the simpler C2C12 cell line model are predictive for effects in vivo.

The hindlimb muscle and liver triglyceride content was measured after gAcrp30 treatment of mice. Hind limb muscles as well as liver samples were removed from treated and untreated animals and the triglyceride and free fatty acid concentration was determined following a standard lipid extraction method (Shimabukuro et al (1997) Proc Natl Acad Sci USA 94:4637-4641, hereby incorporated herein by reference in its entirety including any figures, drawings, or tables) followed by TG and FFA analysis using standard test kits.

Short-term treatment of animals with gAcrp30 (2 injections of 25 µg each given within 3 hours before sacrifice) did not change the triglyceride content either of hind limb muscle or liver tissue. However, after 3 days of treatment, during which period normal C57BL/6J mice consumed a regular rodent diet, mice that had received 25 µg of gAcrp30 twice daily showed significantly higher (p=0.002) muscle triglyceride content (FIG. 5A) than those receiving saline (control: light gray; gAcrp30: dark gray). This contrasted with a lack of increase in liver triglycerides (FIG. 5B). Furthermore, no detectable increase in muscle TG was observed after the 16-day treatment shown independently by directly measuring the muscle TG content and by oil red O staining of frozen microscope sections. In summary, the data indicate that the increase in TG content was transient.

Ketone bodies (KB) are produced in the liver as a result of free fatty acid oxidation, but KB formation does not occur significantly in muscle. In mice receiving the high fat test meal and saline injection, the level of plasma KB increased significantly over the next 3 hours (183±12%, n=6). Animals treated with gAcrp30, on the other hand, showed no increase in plasma KB concentrations. Although not wishing to be limited by any particular theory, this suggests that gAcrp30 inhibits either directly KB formation or can decrease KB production by inhibiting liver FFA oxidation.

Example 5

Methods of Testing the Effect of gOBG3 on Apoptosis

Prior experiments indicated that gAcrp30 either increased cell division or decreased apoptosis is C2C12 cells undergoing differentiation (Example 1). In order to assess the effect C2C12 cells can be transferred into medium containing 0.5% horse serum (rather than 2% horse serum for differentiation), which rapidly induces the onset of apoptosis (Wang & Walsh (1996) hereby incorporated herein by reference in its entirety including any figures, tables, or drawings). Cells would then be incubated for 16 hours either in the presence or absence of gACRP30 and then the level of apoptosis compared by staining for ApopTag as described in Wang & Walsh (1996).

Example 6

Methods of Assessing the Acceleration of Myoblast Differentiation with gOBG3

Prior experiments have also indicated that gAcrp30 accelerates re-organization/reorientation and differentiation of C2C12 muscle cells in vitro (Example 1). Rapid, highly sensitive methods are available to facilitate screening of the activity of variants of gAcrp30 (and antagonists and agonists) for their effect on differentiation. These assays, include, among others, a TaqMan PCR-based method that assesses mRNA levels of muscle-specific markers of differentiation, inlcuding, but not limited to, muscle regulatory factor, myogen, alpha-actin, thermoregulatory uncoupling protein (UCP2), glucose transporter isotype glut4, myf5, beta-actin, UCP1, UCP3, and glut1 (Shimokawa et al (1998) Biochem Biophys Res Commun 246:287-292, hereby incorporated by reference herein in its entirety including any figures, drawings, or tables). Levels of mRNA would be compared between the gAcrp30 treated and the untreated cultures of differentiating C2C12 cells.

Example 7

Effect of gOBG3 on Muscle Cells in Vivo

Experiments can be performed on normal mice as well as mice fed a high fat diet, to assess increases in the differentiation of muscle cells over a time course of treatment using the TaqMan PCR-based method described in Example 6, for example. Other muscle cell parameters discussed herein can also be assessed over time. The animal experiments can be performed as follows, for example:

Experiment 1: 10-week-old male C57BL/6J mice were put on a very high fat/sucrose purified diet for 19 days to promote weight gain (see Example 4); the average body weight at this time was 30 g. The mice were then surgically implanted with an osmotic pump (Alzet, Newark, Del.) delivering either 2.5 μg/day of gAcrp30, 5 μg/day of Acrp30, or physiological saline. The mice were continued on the high fat diet and their body weight was recorded over the following 10-day period. Muscle parameters can be assessed over this same time period.

Experiment 2: mature 9 month old, male obese C57BL/6J mice that had been on the same high fat/sucrose diet for 6 months; the average body weight when the study began was 52.5±0.8 g. Three groups of 8 mice were treated with saline, Acrp30 or gAcrp30 for 16 days. Animals in the treated group received twice daily 25 μg of protein subcutaneously. Body weights were recorded at appropriate time points (daily or weekly). Muscle parameters can also be assessed over the same time period.

Example 8

Mouse Models of Muscular Dystrophy

In order to further assess the efficacy of gAcrp30 and analogs, variants, and fragments thereof (as well as antagonists or agonists as needed) mouse models of muscular dystrophy can be used including, but not limited to, 129P1/ReJ-Lama2$^{dy}$, C57BL/10ScSn-Dmd$^{mdx}$/J, C57BL/6J-Lama2$^{dy}$, C57BL/6J-Lama2$^{dy-2J}$, C57BL/6Ros-Dmd$^{mdx-2Cv}$, C57BL/6Ros-Dmd$^{mdx-3Cv}$, C57BL/6Ros-Dmd$^{mdx-4cv}$, C57BL/6Ros-Dmd$^{mdx52Cv}$, and D.B/Ei-Lama2$^{dy-6J}$/+, all of which are available from Jackson Laboratories. The experiments would include beginning to treat mice as young as possible (and then starting at increasingly later time points) with gAcrp30 as described in Example 7 and comparing the onset and severity of disease symptoms with untreated mice.

Example 9

Cellular Binding and Uptake of gOBG-3 as Detected by Fluorescence Microscopy Fluorecein isothiocyanate (FITC) conjugation of gOBG3: Purified gOBG3 at 1 mg/mL concentration was labeled with FITC using Sigma's FluoroTag FITC conjugation kit (Stock No. FITC-1). Protocol outlined in the Sigma Handbook for small scale conjugation was followed for gOBG3 labeling.

Cell Culture: C2C12 mouse skeletal muscle cells (ATCC, Manassas, Va. CRL-1772) and Hepa-1-6 mouse hepatocytes (ATCC, Manassas, Va. CRL-1830) were seeded into 6 well plates at a cell density of $2 \times 10^5$ cells per well. C2C12 and Hepa-1-6 cells were cultured according to repository's instructions for 24-48 hours prior to analysis. Assay was performed when cells were 80% confluent.

FITC labeled gOBG3 cellular binding and uptake using microscopy in C2C12 and Hepa 1-6 cells. FITC-gOBG3 (50 nM/mL) was added to each cell culture well. Cells were incubated for 1 hour at 37° C., 5% $CO_2$. Cells were Washed 2× with PBS, cells were scraped from well into 1 mL of PBS. Cell suspension was transferred to an eppendorf tube and centrifuged at 1000 rpm for 2 minutes. Supernatant was removed and cells resuspended in 200 μL of PBS. Binding and uptake of FITC-gOBG3 was analyzed by fluorescence microscopy under 40× magnification.

Analysis of C2C12 and Hepa 1-6 cells reveals identical phenotypes with respect to FITC-gOBG3 binding and uptake profiles. FITC-gOBG3 appears to be localized within vesicles in the cytoplasm of both mouse hepatocytes and mouse myoblasts, suggesting that binding and uptake of FITC-gOBG3 is occurring. Thus, this assay may be useful for identifying agents that facilitate or prevent the uptake and/or binding of OBG3 or gOBG3 polypeptides to cells by adding the substance to be tested with, before, or after the FITC-gOBG3.

Example 10

Detection of Apm-1 Fragment in Human Plasma after Immunoprecipitation

Figures 6A, 6B:
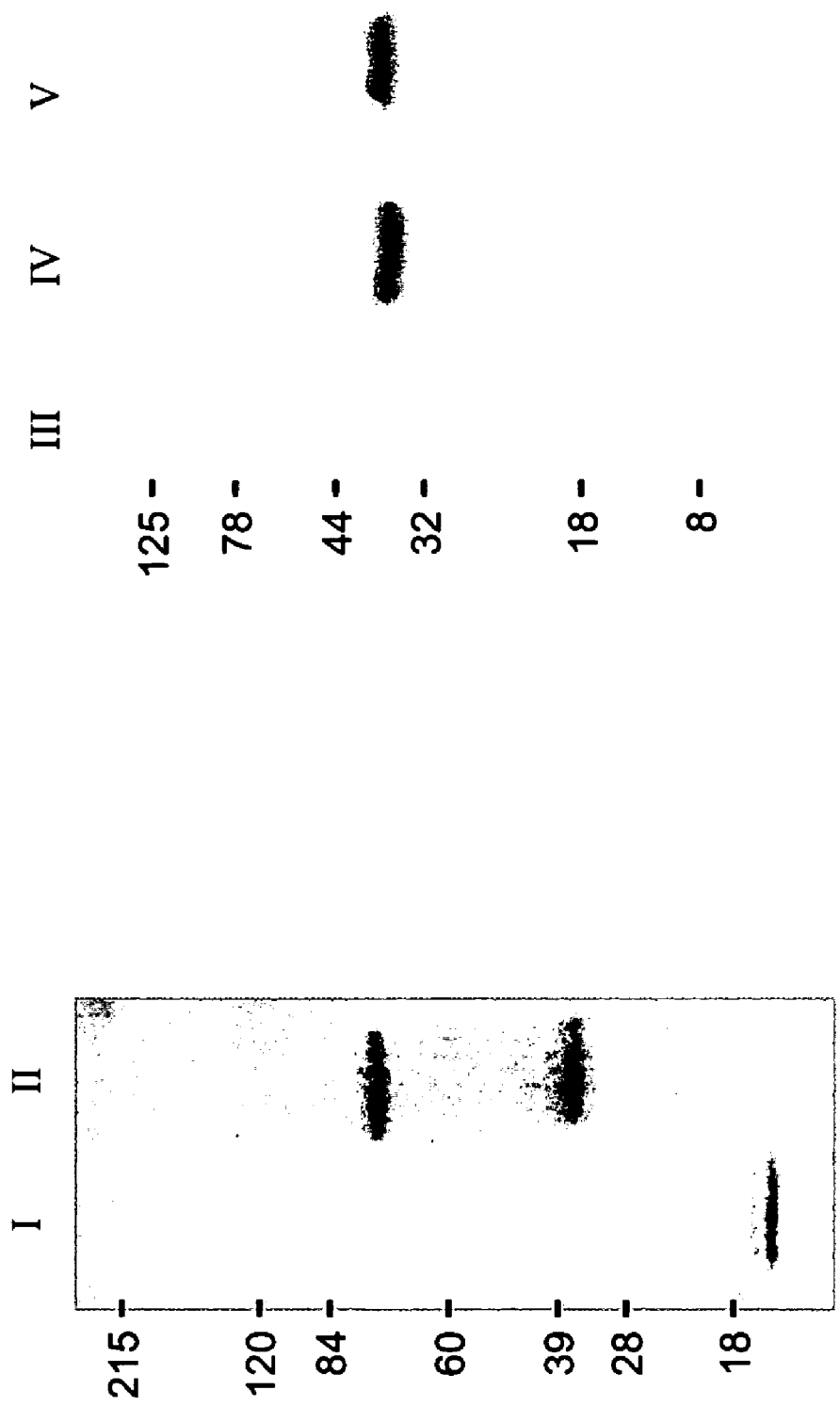
FIGS. 6A and 6B show SDS-PAGE separations of the purification of Acrp30 and gAcrp30 (6A) and a cleavage product of apm1 (6B).

The recombinant form of Acrp30 protein used has an apparent molecular weight of 37 kDa and forms a dimer of 74 kDa (FIG. 6A, Lane II). A proteolytic fragment that contains the entire globular head region (gAcrp30) and that migrates with an apparent molecular weight of 18 kDa was generated using acetylated trypsin (FIG. 6A, lane I). Both protein preparations (Acrp30 and gAcrp30) were essentially endotoxin free; "ActiClean Etox" affinity columns were used to remove potential endotoxin contaminations (Sterogene Bioseparations Inc., Carlsbad, Calif.) following the manufacturer's protocol. Endotoxin levels were determined by Endosafe, Charleston, S.C. As determined by N-terminal sequencing of purified gAcrp30, the site of cleavage was just before amino acid 104.

Immunoprecipitation of human plasma Apm1 followed by Western blotting was used to detect a cleavage product of Apm-1, the human homolog of Acrp30, using a globular head specific anti-serum for the immunoprecipitation step as well as for the detection step. Preimmune serum or serum raised against the globular head domain or human non-homologous region (HDQETTQGPGVLLPLPKGA) were cross-linked to protein A (Sigma Chemical Colo., Saint Louis, Mo.) using dimethyl-pimelimidate-dihydrochloride (Sigma Chemical Co, Saint Louis, Mo.). After washing (0.2 M salt), proteins were eluted from protein A, were separated by SDS-PAGE, and were transferred to Protran® pure nitrocellulose membrane (Schleicher and Schuell, Keene, N.H.) using standard procedures. Apm-1 products were visualized using globular head domain antibodies labeled with biotin; horseradish peroxidase conjugated to Streptavidin and CN/DAB substrate kit (Pierce, Rockford, Ill.) according to manufacturer's instructions.

The apparent molecular weight of this truncated form was 27 kDa, corresponding to about 70% of the complete form of Apm-1 (FIG. 6B, Lane IV). This truncated form was not detectable when immunoprecipitation was performed using a different antibody directed against the human non-homologous region (HDQETTTQGPGVLLPLPKGA) of Apm-1; this domain is located toward the $NH_2$ terminal end of the protein outside of the globular domain (FIG. 6, Lane V). Both anti-Apm-1 antibodies directed against either the globular or the non-globular domain identified the full-length form of the protein, as well as a low abundance dimer of apparent MW 74 kDa.

Example 11

Tissue Distribution of gAcrp30

Intra Venous Injection of $^{251}$I (g)Acrp30

The disappearance from plasma and subsequent tissue distribution of Acrp30 and the globular head (gAcrp30) was investigated by injecting $^{125}$I (g)Acrp30 into CD-1 mice.

CD-1 mice were kept on regular diet with free access to food and water. The day/night light cycle was kept at 12 hr ON/12 hr OFF. Acrp30 and gACRP30 were prepared as previously described and labeled with $^{125}$I to a specific activity of approximately 100 cpm/ng using Iodobeads (Pierce). The labeled protein was prepared immediately before injection and 0.1-0.5 μCi were injected through the tail vein. Clearance of the labeled protein from plasma was followed over 3 hrs after which the animals were perfused systemically with PBS+EDTA to remove all blood. Tissues were isolated (liver, adipose, kidney, skeletal muscle, brain), weighed, and the specific activity in plasma and tissue was determined.

Acrp30 showed a plasma half-life of about 7 hours. The plasma turnover of gAcrp30 was significantly faster showing a half-life close to 1 hour. The majority of the labeled Acrp3.0 protein was found in kidney and in skeletal muscle tissue, indicating that it represents a functional target tissue. A much smaller part of the injected protein was found in adipose and liver tissue and only a very small pool was seen in brain.

Immunohistochemistrey Studies

Frozen sections of skeletal muscle from mice were stained using an antibody to the globular head of Acrp30 coupled with colorimetric detection. Briefly, C57 mice were sacrificed and various skeletal muscles were isolated. Muscles were frozen in an isopentane/liquid nitrogen bath. Tissue was then sectioned at 8 microns using a Leica 3050 cryostat and sections were picked up on microscope slides. Slides were dried overnight and fixed with 4° C. acetone after which sections were pretreated for endogenous peroxidase and biotin prior to IHC. An antibody to gAcrp30 was used on the slides at a concentration of 1:20,000. The primary antibody was detected using a biotin-labeled streptavidin system. The chromagen was DAB with hematoxylin counterstain Cross-sectional views of skeletal muscle show distinct outlining of muscle fibers with Acrp30 staining. A positive signal is also seen in any blood vessels in the tissue. This is not surprising since the animals were not perfused before tissues were isolated and Acrp30 should thus be present in the plasma that would be in these vessels. This staining appears to be specific given that tissues stained with preimmune at the same concentration were clean. Also it should be noted that tissues without much Acrp30, such as liver, do not show much Acrp30 staining.

The substantial presence of Acrp30 in skeletal muscle supports the inventor's belief that muscle is in fact a target tissue of this molecule.

REFERENCES

Dehouck et al. J Neurochem 54:1798-801, 1990
Shapiro, and Scherer, Curr. Biol. 8:335-338, 1998
Uysal, et al. Nature 389:610-614, 1997

The invention claimed is:

1. A method of accelerating skeletal muscle cell differentiation, comprising contacting skeletal muscle cells in vitro with gOBG3 polypeptides consisting of: amino acids 101-244 of SEQ ID NO: 6, amino acids 108-244 of SEQ ID NO: 6, amino acids 104-247 of SEQ ID NOs: 2 or 4, or amino acids 111-247 of SEQ ID NOs: 2 or 4, or variants thereof comprising polyethylene glycol conjugated to gOBG3 polypeptides consisting of: amino acids 101-244 of SEQ ID NO: 6, amino acids 108-244 of SEQ ID NO: 6, amino acids 104-247 of SEQ ID NOs: 2 or 4, or amino acids 111-247 of SEQ ID NOs: 2 or 4, wherein said gOBG3 accelerates the differentiation of said cells.

2. A method of accelerating skeletal muscle cell realignment in relation to other skeletal muscle cells in vitro, comprising contacting skeletal muscle cells in vitro with gOBG3 polypeptides consisting of: amino acids 101-244 of SEQ ID NO: 6, amino acids 108-244 of SEQ ID NO: 6, amino acids 104-247 of SEQ ID NOs: 2or 4, or amino acids 111-247 of SEQ ID NOs: 2 or 4, or variants thereof comprising polyethylene glycol conjugated to gOBG3 polypeptides consisting of: amino acids 101-244 of SEQ ID NO: 6, amino acids 108-244 of SEQ ID NO: 6, amino acids 104-247 of SEQ ID NOs: 2 or 4, or amino acids 111-247 of SEQ ID NOs: 2 or 4 in an amount sufficient to accelerate the realignment of said skeletal muscle cells in relation to each other.

3. A method of treating skeletal muscle cell disorders selected from the group consisting of muscle-related recovery after injuries, muscle-related recovery after surgery, and muscle wasting in an individual, comprising diagnosing an individual as having a skeletal muscle cell disorder selected from the group consisting of muscle-related recovery after injuries, muscle-related recovery after surgery, and muscle wasting and administering to said diagnosed individual an amount of gOBG3 polypeptide consisting of: amino acids 101-244 of SEQ ID NO: 6, amino acids 108-244 of SEQ ID NO: 6, amino acids 104-247 of SEQ ID NOs: 2 or 4, amino acids 111-247 of SEQ ID NOs: 2 or 4, or variants thereof comprising polyethylene glycol conjugated to gOBG3 polypeptides consisting of: amino acids 101-244 of SEQ ID NO: 6, amino acids 108-244 of SEQ ID NO: 6, amino acids 104-247 of SEQ ID NOs: 2 or 4, or amino acids 111-247 of SEQ ID NOs: 2 or 4 sufficient to accelerate the reorganization and alignment of said cells in relation to each other and treat said disorder.

4. A method of treating skeletal muscle injury comprising selecting an individual having a skeletal muscle injury and administering to an individual in need thereof a therapeutically effective dose of gOBG3 polypeptide, said gOBG3 polypeptide consisting of: amino acids 101-244 of SEQ ID NO: 6, amino acids 108-244 of SEQ ID NO: 6, amino acids 104-247 of SEQ ID NOs: 2 or 4, or amino acids 111-247 of SEQ ID NOs: 2 or 4, or variants thereof comprising polyethyleneglycol conjugated to gOBG3 polypeptides consisting of: amino acids 101-244 of SEQ ID NO: 6, amino acids 108-244 of SEQ ID NO: 6, amino acids 104-247 of SEQ ID NOs: 2 or 4, or amino acids 111-247 of SEQ ID NOs: 2 or 4, wherein said therapeutically effective dose is sufficient for treating said skeletal muscle injury.

5. The method according to claim 4, wherein said skeletal muscle injury is trauma.

6. The method according to claim 5, wherein said trauma is due to accident, surgery or over-exercise.

7. The method according to claim 6, wherein said trauma is surgery.

8. The method according to claim 6, wherein said trauma is due to accident.

9. The method according to claim 4, wherein said gOBG3 polypeptides consist of amino acids 101-244 of SEQ ID NO: 6.

10. The method according to claim 4, wherein said gOBG3 polypeptides consist of amino acids 108-244 of SEQ ID NO: 6.

11. The method according to claim 4, wherein said gOBG3 variant comprises polyethylene glycol conjugated to gOBG3 polypeptides consisting of amino acids 101-244 of SEQ ID NO: 6.

12. The method according to claim 4, wherein said gOBG3 variant comprises polyethylene glycol conjugated to gOBG3 polypeptides consisting of amino acids 108-244 of SEQ ID NO: 6.

13. A method of treating a skeletal muscle disorder comprising diagnosing an individual as having a skeletal muscle disorder and administering to said diagnosed individual a therapeutically effective dose of gOBG3 polypeptide, said gOBG3 polypeptide consisting of: amino acids 101-244 of SEQ ID NO: 6, amino acids 108-244 of SEQ ID NO: 6, amino acids 104-247 of SEQ ID NOs: 2 or 4, amino acids 111-247 of SEQ ID NOs: 2 or 4, orvariants thereof comprising polyethylene glycol conjugated to gOBG3 polypeptides consisting of: amino acids 101-244 of SEQ ID NO: 6, amino acids 108-244 of SEQ ID NO: 6, amino acids 104-247 of SEQ ID NOs: 2 or 4, or amino acids 111-247 of SEQ ID NOs: 2 or 4, wherein said effective dose is sufficient for treating said skeletal muscle disorder.

14. The method according to claim 13, wherein said gOBG3 polypeptides consist of amino acids 101-244 of SEQ ID NO: 6.

15. The method according to claim 13, wherein said gO13G3 polypeptides consist of amino acids 108-244 of SEQ ID NO: 6.

16. The method according to claim 13, wherein said gOBG3 variant comprises polyethylene glycol conjugated to gOBG3 polypeptides consisting of amino acids 101-244 of SEQ ID NO: 6.

17. The method according to claim 13, wherein said gOBG3 variant comprises polyethylene glycol conjugated to gOBG3 polypeptides consisting of amino acids 108-244 of SEQ ID NO: 6.

18. The method according to claim 1, wherein said gOBG3 polypeptides consist of amino acids 101-244 of SEQ ID NO: 6.

19. The method according to claim 1, wherein said gOBG3 polypeptides consist of amino acids 108-244 of SEQ ID NO: 6.

20. The method according to claim 1, wherein said gOBG3 polypeptides consist of amino acids 104-247 of SEQ ID NO: 2.

21. The method according to claim 1, wherein said gOBG3 variant comprises polyethylene glycol conjugated to gOBG3 polypeptides consisting of amino acids 101-244 of SEQ ID NO: 6.

22. The method according to claim 1, wherein said gOBG3 variant comprises polyethylene glycol conjugated to gOBG3 polypeptides consisting of amino acids 108-244 of SEQ ID NO: 6.

23. The method according to claim 1, wherein said gOBG3 variant comprises polyethylene glycol conjugated to gOBG3 polypeptides consisting of amino acids 104-247 of SEQ ID NO: 2.

24. The method according to claim 1, wherein said gOBG3 variant comprises polyethylene glycol conjugated to gOBG3 polypeptides consisting of amino acids 111-247 of SEQ ID NO: 2.

25. The method according to claim 2, wherein said gOBG3 polypeptides consist of amino acids 101-244 of SEQ ID NO: 6.

26. The method according to claim 2, wherein said gOBG3 polypeptides consist of amino acids 108-244 of SEQ ID NO: 6.

27. The method according to claim 2, wherein said gOBG3 polypeptides consist of amino acids 104-247 of SEQ ID NO: 2.

28. The method according to claim 2, wherein said gOBG3 polypeptides consist of amino acids 111-247 of SEQ ID NO: 2.

29. The method according to claim 2, wherein said gOBG3 variant comprises polyethylene glycol conjugated to gOBG3 polypeptides consisting of amino acids 101-244 of SEQ ID NO: 6.

30. The method according to claim 2, wherein said gOBG3 variant comprises polyethylene glycol conjugated to gOBG3 polypeptides consisting of amino acids 108-244 of SEQ ID NO: 6.

31. The method according to claim 2, wherein said gOBG3 variant comprises polyethylene glycol conjugated to gOBG3 polypeptides consisting of amino acids 104-247 of SEQ ID NO: 2.

32. The method according to claim 2, wherein said gOBG3 polypeptides consist of amino acids 111-247 of SEQ ID NO: 2.

33. The method according to claim 3, wherein said gOBG3 polypeptides consist of amino acids 101-244 of SEQ ID NO: 6.

34. The method according to claim 3, wherein said gOBG3 polyethylene consist of amino acids 108-244 of SEQ ID NO: 6.

35. The method according to claim 3, wherein said gOBG3 variant comprises polyethylene glycol conjugated to gOBG3 polypeptides consisting of amino acids 101-244 of SEQ ID NO: 6.

36. The method according to claim 3, wherein said gOBG3 variant comprises polyethylene glycol conjugated to gOBG3 polypeptides consisting of amino acids 108-244 of SEQ ID NO: 6.

* * * * *

UNITED STATES PATENT AND TRADEMARK OFFICE
CERTIFICATE OF CORRECTION

PATENT NO. : 7,405,193 B2
APPLICATION NO. : 10/296865
DATED : July 29, 2008
INVENTOR(S) : Harvey Lodish et al.

It is certified that error appears in the above-identified patent and that said Letters Patent is hereby corrected as shown below:

<u>Column 5,</u>
Line 9, "six-flame" should read --six-frame--.

<u>Column 17,</u>
Line 25, "40 μg" should read --40 μL/g--.
Line 26, "1.0 mg/mL" should read --10 mg/mL--.

<u>Column 18,</u>
Line 46, "521-5351" should read --521-531--.

<u>Column 23,</u>
Line 1, "HDQETTQGPGVLLPLPKGA" should read
    --HDQETTTQGPGVLLPLPKGA--.
Line 30, "of $^{251}$I" should read --of $^{125}$I--.

<u>Column 24,</u>
Line 5, "Acrp3.0" should read --Acrp30--.

<u>Column 62,</u>
Line 22, "orvariants" should read --or variants--.
Line 33, "gO13G3" should read --gOBG3--.

UNITED STATES PATENT AND TRADEMARK OFFICE
CERTIFICATE OF CORRECTION

PATENT NO. : 7,405,193 B2
APPLICATION NO. : 10/296865
DATED : July 29, 2008
INVENTOR(S) : Harvey Lodish et al.

It is certified that error appears in the above-identified patent and that said Letters Patent is hereby corrected as shown below:

Column 64,
Lines 5-7, "32. The method according to claim 2, wherein said gOBG3 polypeptides consist of amino acids 111-247 of SEQ ID NO: 2." should read
--32. The method according to claim 2, wherein said gOBG3 variant comprises polyethylene glycol conjugated to gOBG3 polypeptides consisting of amino acids 111-247 of SEQ ID NO: 2--.
Line 12, "polyethylene" should read --polypeptides--.

Signed and Sealed this

Twenty-third Day of December, 2008

JON W. DUDAS
*Director of the United States Patent and Trademark Office*

SEQUENCE LISTING

<160> NUMBER OF SEQ ID NOS: 7

<210> SEQ ID NO 1
<211> LENGTH: 1152
<212> TYPE: DNA
<213> ORGANISM: mus musculus

<400> SEQUENCE: 1

```
gaattcggca cgaggg atg cta ctg ttg caa gct ctc ctg ttc ctc tta atc      52
               Met Leu Leu Leu Gln Ala Leu Leu Phe Leu Leu Ile
                 1               5                      10 ctg ccc agt cat gcc gaa gat gac gtt act aca act gaa gag cta gct      100
Leu Pro Ser His Ala Glu Asp Asp Val Thr Thr Thr Glu Glu Leu Ala
         15                  20                  25 cct gct ttg gtc cct cca ccc aag gga act tgt gca ggt tgg atg gca      148
Pro Ala Leu Val Pro Pro Pro Lys Gly Thr Cys Ala Gly Trp Met Ala
     30                  35                  40
```

-continued

| | | |
|---|---|---|
| ggc atc cca gga cat tct ggc cac aat ggc aca cca ggc cgt gat ggc<br>Gly Ile Pro Gly His Ser Gly His Asn Gly Thr Pro Gly Arg Asp Gly<br>45                    50                    55                    60 | 196 |
| aga gat ggc act cct gga gag aag gga gag aaa gga gat tca ggt ctt<br>Arg Asp Gly Thr Pro Gly Glu Lys Gly Glu Lys Gly Asp Ser Gly Leu<br>                  65                    70                    75 | 244 |
| ctt ggt cct aag ggt gag aca gga gat gtt gga atg aca gga gct gaa<br>Leu Gly Pro Lys Gly Glu Thr Gly Asp Val Gly Met Thr Gly Ala Glu<br>             80                    85                    90 | 292 |
| ggg cct cgg ggc ttc ccc gga acc cct ggc agg aaa gga gag cct gga<br>Gly Pro Arg Gly Phe Pro Gly Thr Pro Gly Arg Lys Gly Glu Pro Gly<br>       95                    100                  105 | 340 |
| gaa gcc gct tat gtg tat cgc tca ggc ttc agt gtg ggg ctg gag acc<br>Glu Ala Ala Tyr Val Tyr Arg Ser Gly Phe Ser Val Gly Leu Glu Thr<br>110                    115                    120 | 388 |
| cgc gtc act gtt ccc aat gta ccc att cgc ttt act aag atc ttc tac<br>Arg Val Thr Val Pro Asn Val Pro Ile Arg Phe Thr Lys Ile Phe Tyr<br>125                    130                    135                    140 | 436 |
| aac caa cag aat cat tat gac aac agc act ggc aag ttc tac tgc aac<br>Asn Gln Gln Asn His Tyr Asp Asn Ser Thr Gly Lys Phe Tyr Cys Asn<br>                  145                    150                    155 | 484 |
| att ccg gga ctc tac tac ttc tct tac cac atc acg gtg tac atg aaa<br>Ile Pro Gly Leu Tyr Tyr Phe Ser Tyr His Ile Thr Val Tyr Met Lys<br>                    160                    165                    170 | 532 |
| gat gtg aag gtg agc ctc ttc aag aag gac aag gcc gtt ctc ttc acc<br>Asp Val Lys Val Ser Leu Phe Lys Lys Asp Lys Ala Val Leu Phe Thr<br>175                    180                    185 | 580 |
| tac gac cag tat cag gaa aag aat gtg gac cag gcc tct ggc tct gtg<br>Tyr Asp Gln Tyr Gln Glu Lys Asn Val Asp Gln Ala Ser Gly Ser Val<br>          190                    195                    200 | 628 |
| ctc ctc cat ctg gag gtg gga gac caa gtc tgg ctc cag gtg tat ggg<br>Leu Leu His Leu Glu Val Gly Asp Gln Val Trp Leu Gln Val Tyr Gly<br>205                  210                    215                    220 | 676 |
| gat ggg gac cac aat gga ctc tat gca gat aac gtc aac gac tct aca<br>Asp Gly Asp His Asn Gly Leu Tyr Ala Asp Asn Val Asn Asp Ser Thr<br>                  225                    230                    235 | 724 |
| ttt act ggc ttt ctt ctc ttc cat gat acc aac tga ctgcaactac<br>Phe Thr Gly Phe Leu Leu Phe His Asp Thr Asn<br>240                    245 | 770 |
| tcatagccca taccagga gaatcatgga acgtcgacac actttcagct tagtttgaga | 830 |
| gattgatttt attgcttagt ttgagagtcc tgagtattat ccacacgtgt actcacttgt | 890 |
| tcattaaacg actttataaa aaataatttg tgttcctagt ccagaaaaaa aggcactccc | 950 |
| tggtctccac gactcttaca tggtagcaat aacagaatga aaatcacatt tggtatgggg | 1010 |
| gcttacaat attcgcatga ctgtctggaa gtagaccatg ctattttct gctcactgta | 1070 |
| cacaaatatt gttcacataa accctataat gtaaatatga aatacagtga ttatcttctc | 1130 |
| aaaaaaaact cgtgccgaat tc | 1152 |

<210> SEQ ID NO 2
<211> LENGTH: 247
<212> TYPE: PRT
<213> ORGANISM: mus musculus

<400> SEQUENCE: 2

Met Leu Leu Leu Gln Ala Leu Leu Phe Leu Leu Ile Leu Pro Ser His
1                   5                   10                 15

Ala Glu Asp Asp Val Thr Thr Thr Glu Glu Leu Ala Pro Ala Leu Val
                20                   25               30

```
Pro Pro Pro Lys Gly Thr Cys Ala Gly Trp Met Ala Gly Ile Pro Gly
            35                  40                  45

His Ser Gly His Asn Gly Thr Pro Gly Arg Asp Gly Arg Asp Gly Thr
    50                  55                  60

Pro Gly Glu Lys Gly Glu Lys Gly Asp Ser Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
                100                 105                 110

Val Tyr Arg Ser Gly Phe Ser Val Gly Leu Glu Thr Arg Val Thr Val
            115                 120                 125

Pro Asn Val Pro Ile Arg Phe Thr Lys Ile Phe Tyr Asn Gln Gln Asn
        130                 135                 140

His Tyr Asp Asn Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
                180                 185                 190

Gln Glu Lys Asn Val Asp Gln Ala Ser Gly Ser Val Leu Leu His Leu
            195                 200                 205

Glu Val Gly Asp Gln Val Trp Leu Gln Val Tyr Gly Asp Gly Asp His
210                 215                 220

Asn Gly Leu Tyr Ala Asp Asn Val Asn Asp Ser Thr Phe Thr Gly Phe
225                 230                 235                 240

Leu Leu Phe His Asp Thr Asn
                245

<210> SEQ ID NO 3
<211> LENGTH: 1276
<212> TYPE: DNA
<213> ORGANISM: mus musculus

<400> SEQUENCE: 3
ctctaaagat tgtcagtgga tctgacgaca ccaaaagggc tcagg atg cta ctg ttg     57
                                                Met Leu Leu Leu
                                                1 caa gct ctc ctg ttc ctc tta atc ctg ccc agt cat gcc gaa gat gac    105
Gln Ala Leu Leu Phe Leu Leu Ile Leu Pro Ser His Ala Glu Asp Asp
5                   10                  15                  20 gtt act aca act gaa gag cta gct cct gct ttg gtc cct cca ccc aag    153
Val Thr Thr Thr Glu Glu Leu Ala Pro Ala Leu Val Pro Pro Pro Lys
                25                  30                  35 gga act tgt gca ggt tgg atg gca ggc atc cca gga cat cct ggc cac    201
Gly Thr Cys Ala Gly Trp Met Ala Gly Ile Pro Gly His Pro Gly His
            40                  45                  50 aat ggc aca cca ggc cgt gat ggc aga gat ggc act cct gga gag aag    249
Asn Gly Thr Pro Gly Arg Asp Gly Arg Asp Gly Thr Pro Gly Glu Lys
        55                  60                  65 gga gag aaa gga gat gca ggt ctt ctt ggt cct aag ggt gag aca gga    297
Gly Glu Lys Gly Asp Ala Gly Leu Leu Gly Pro Lys Gly Glu Thr Gly
    70                  75                  80 gat gtt gga atg aca gga gct gaa ggg cca cgg ggc ttc ccc gga acc    345
Asp Val Gly Met Thr Gly Ala Glu Gly Pro Arg Gly Phe Pro Gly Thr
85                  90                  95                  100
```

| | | |
|---|---|---|
| cct ggc agg aaa gga gag cct gga gaa gcc gct tat atg tat cgc tca<br>Pro Gly Arg Lys Gly Glu Pro Gly Glu Ala Ala Tyr Met Tyr Arg Ser<br>                105                      110                  115 | 393 |
| gcg ttc agt gtg ggg ctg gag acc cgc gtc act gtt ccc aat gta ccc<br>Ala Phe Ser Val Gly Leu Glu Thr Arg Val Thr Val Pro Asn Val Pro<br>        120                      125                      130 | 441 |
| att cgc ttt act aag atc ttc tac aac caa cag aat cat tat gac ggc<br>Ile Arg Phe Thr Lys Ile Phe Tyr Asn Gln Gln Asn His Tyr Asp Gly<br>            135                      140                      145 | 489 |
| agc act ggc aag ttc tac tgc aac att ccg gga ctc tac tac ttc tct<br>Ser Thr Gly Lys Phe Tyr Cys Asn Ile Pro Gly Leu Tyr Tyr Phe Ser<br>150                      155                      160 | 537 |
| tac cac atc acg gtg tac atg aaa gat gtg aag gtg agc ctc ttc aag<br>Tyr His Ile Thr Val Tyr Met Lys Asp Val Lys Val Ser Leu Phe Lys<br>165                      170                      175                  180 | 585 |
| aag gac aag gcc gtt ctc ttc acc tac gac cag tat cag gaa aag aat<br>Lys Asp Lys Ala Val Leu Phe Thr Tyr Asp Gln Tyr Gln Glu Lys Asn<br>                185                      190                      195 | 633 |
| gtg gac cag gcc tct ggc tct gtg ctc ctc cat ctg gag gtg gga gac<br>Val Asp Gln Ala Ser Gly Ser Val Leu Leu His Leu Glu Val Gly Asp<br>        200                      205                      210 | 681 |
| caa gtc tgg ctc cag gtg tat ggg gat ggg gac cac aat gga ctc tat<br>Gln Val Trp Leu Gln Val Tyr Gly Asp Gly Asp His Asn Gly Leu Tyr<br>            215                      220                      225 | 729 |
| gca gat aac gtc aac gac tct aca ttt act ggc ttt ctt ctc tac cat<br>Ala Asp Asn Val Asn Asp Ser Thr Phe Thr Gly Phe Leu Leu Tyr His<br>230                      235                      240 | 777 |
| gat acc aac tga ctgcaactac ccatagccca tacaccagga gaatcatgga<br>Asp Thr Asn<br>245 | 829 |
| acagtcgaca cactttcagc ttagtttgag agattgattt tattgcttag tttgagagtc | 889 |
| ctgagtatta tccacacgtg tactcacttg ttcattaaac gactttataa aaataatttt | 949 |
| gtgttcctag tccagaaaaa aaggcactcc ctggtctcca cgactcttac atggtagcaa | 1009 |
| taacagaatg aaaatcacat ttggtatggg ggcttcacaa tattcgcatg actgtctgga | 1069 |
| agtagaccat gctatttttc tgctcactgt acacaaatat tgttcacata aaccctataa | 1129 |
| tgtaaatatg aaatacagtg attactcttc tcacaggctg agtgtatgaa tgtctaaaga | 1189 |
| cccataagta ttaaagtggt agggataaat tggaaaaaaa aaaaaaaaa aagaaaaact | 1249 |
| ttagagcaca ctggcggccg ttactag | 1276 |

<210> SEQ ID NO 4
<211> LENGTH: 247
<212> TYPE: PRT
<213> ORGANISM: mus musculus

<400> SEQUENCE: 4

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Pro Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65                  70                  75                  80

-continued

```
Gly Glu Thr Gly Asp Val Gly Met Thr Gly Ala Gly Pro Arg Gly
             85                  90                  95
Phe Pro Gly Thr Pro Gly Arg Lys Gly Glu Pro Gly Glu Ala Ala Tyr
            100                 105                 110
Met Tyr Arg Ser Ala Phe Ser Val Gly Leu Glu Thr Arg Val Thr Val
        115                 120                 125
Pro Asn Val Pro Ile Arg Phe Thr Lys Ile Phe Tyr Asn Gln Gln Asn
130                 135                 140
His Tyr Asp Gly Ser Thr Gly Lys Phe Tyr Cys Asn Ile Pro Gly Leu
145                 150                 155                 160
Tyr Tyr Phe Ser Tyr His Ile Thr Val Tyr Met Lys Asp Val Lys Val
                165                 170                 175
Ser Leu Phe Lys Lys Asp Lys Ala Val Leu Phe Thr Tyr Asp Gln Tyr
            180                 185                 190
Gln Glu Lys Asn Val Asp Gln Ala Ser Gly Ser Val Leu Leu His Leu
        195                 200                 205
Glu Val Gly Asp Gln Val Trp Leu Gln Val Tyr Gly Asp Gly Asp His
    210                 215                 220
Asn Gly Leu Tyr Ala Asp Asn Val Asn Asp Ser Thr Phe Thr Gly Phe
225                 230                 235                 240
Leu Leu Tyr His Asp Thr Asn
                245
```

<210> SEQ ID NO 5
<211> LENGTH: 4517
<212> TYPE: DNA
<213> ORGANISM: Homo sapiens

<400> SEQUENCE: 5

```
ctgattccat accagagggg ctcagg atg ctg ttg ctg gga gct gtt cta ctg      53
                         Met Leu Leu Leu Gly Ala Val Leu Leu
                           1               5 cta tta gct ctg ccc ggg cat gac cag gaa acc acg act caa ggg ccc     101
Leu Leu Ala Leu Pro Gly His Asp Gln Glu Thr Thr Thr Gln Gly Pro
10                  15                  20                  25 gga gtc ctg ctt ccc ctg ccc aag ggg gcc tgc aca ggt tgg atg gcg     149
Gly Val Leu Leu Pro Leu Pro Lys Gly Ala Cys Thr Gly Trp Met Ala
                30                  35                  40 ggc atc cca ggg cat ccg ggc cat aat ggg gcc cca ggc cgt gat ggc     197
Gly Ile Pro Gly His Pro Gly His Asn Gly Ala Pro Gly Arg Asp Gly
            45                  50                  55 aga gat ggc acc cct ggt gag aag ggt gag aaa gga gat cca ggt ctt     245
Arg Asp Gly Thr Pro Gly Glu Lys Gly Glu Lys Gly Asp Pro Gly Leu
        60                  65                  70 att ggt cct aag gga gac atc ggt gaa acc gga gta ccc ggg gct gaa     293
Ile Gly Pro Lys Gly Asp Ile Gly Glu Thr Gly Val Pro Gly Ala Glu
    75                  80                  85 ggt ccc cga ggc ttt ccg gga atc caa ggc agg aaa gga gaa cct gga     341
Gly Pro Arg Gly Phe Pro Gly Ile Gln Gly Arg Lys Gly Glu Pro Gly
90                  95                 100                 105 gaa ggt gcc tat gta tac cgc tca gca ttc agt gtg gga ttg gag act     389
Glu Gly Ala Tyr Val Tyr Arg Ser Ala Phe Ser Val Gly Leu Glu Thr
                110                 115                 120 tac gtt act atc ccc aac atg ccc att cgc ttt acc aag atc ttc tac     437
Tyr Val Thr Ile Pro Asn Met Pro Ile Arg Phe Thr Lys Ile Phe Tyr
            125                 130                 135 aat cag caa aac cac tat gat ggc tcc act ggt aaa ttc cac tgc aac     485
Asn Gln Gln Asn His Tyr Asp Gly Ser Thr Gly Lys Phe His Cys Asn
```

-continued

|  | 140 |  |  |  | 145 |  |  |  | 150 |  |  |  |
|---|---|---|---|---|---|---|---|---|---|---|---|---|
| att | cct | ggg | ctg | tac | tac | ttt | gcc | tac | cac | atc | aca | gtc tat atg aag | 533 |
| Ile | Pro | Gly | Leu | Tyr | Tyr | Phe | Ala | Tyr | His | Ile | Thr | Val Tyr Met Lys |
|  | 155 |  |  |  | 160 |  |  |  | 165 |  |  |  |

| gat | gtg | aag | gtc | agc | ctc | ttc | aag | aag | gac | aag | gct | atg ctc ttc acc | 581 |
| Asp | Val | Lys | Val | Ser | Leu | Phe | Lys | Lys | Asp | Lys | Ala | Met Leu Phe Thr |
| 170 |  |  |  | 175 |  |  |  | 180 |  |  |  | 185 |

| tat | gat | cag | tac | cag | gaa | aat | aat | gtg | gac | cag | gcc | tcc ggc tct gtg | 629 |
| Tyr | Asp | Gln | Tyr | Gln | Glu | Asn | Asn | Val | Asp | Gln | Ala | Ser Gly Ser Val |
|  |  | 190 |  |  |  |  | 195 |  |  |  |  | 200 |

| ctc | ctg | cat | ctg | gag | gtg | ggc | gac | caa | gtc | tgg | ctc | cag gtg tat ggg | 677 |
| Leu | Leu | His | Leu | Glu | Val | Gly | Asp | Gln | Val | Trp | Leu | Gln Val Tyr Gly |
|  |  |  | 205 |  |  |  |  | 210 |  |  |  | 215 |

| gaa | gga | gag | cgt | aat | gga | ctc | tat | gct | gat | aat | gac | aat gac tcc acc | 725 |
| Glu | Gly | Glu | Arg | Asn | Gly | Leu | Tyr | Ala | Asp | Asn | Asp | Asn Asp Ser Thr |
|  |  | 220 |  |  |  |  | 225 |  |  |  |  | 230 |

| ttc | aca | ggc | ttt | ctt | ctc | tac | cat | gac | acc | aac | tga | tcaccactaa | 771 |
| Phe | Thr | Gly | Phe | Leu | Leu | Tyr | His | Asp | Thr | Asn |  |  |
|  | 235 |  |  |  |  | 240 |  |  |  |  |  |  |

| ctcagagcct | cctccaggcc | aaacagcccc | aaagtcaatt | aaaggctttc | agtacggtta | 831 |
| ggaagttgat | tattatttag | ttggaggcct | ttagatatta | ttcattcatt | tactcattca | 891 |
| tttattcatt | cattcatcaa | gtaactttaa | aaaaatcata | tgctatgttc | ccagtcctgg | 951 |
| ggagcttcac | aaacatgacc | agataactga | ctagaaagaa | gtagttgaca | gtgctatttt | 1011 |
| gtgcccactg | tctctcctga | tgctcatatc | aatcctataa | ggcacaggga | acaagcattc | 1071 |
| tcctgttttt | acagattgta | tcctgaggct | gagagagtta | agtgaatgtc | taaggtcaca | 1131 |
| cagtattaag | tgacagtgct | agaaatcaaa | cccagagctg | tggactttgt | tcactagact | 1191 |
| gtgccctttt | atagaggtac | atgttctctt | tggagtgttg | gtaggtgtct | gtttcccacc | 1251 |
| tcacctgaga | gccattgaat | ttgccttcct | catgaattaa | aacctccccc | aagcagagct | 1311 |
| tcctcagaga | aagtggttct | atgatgaagt | cctgtcttgg | aaggactact | actcaatggc | 1371 |
| ccctgcacta | ctctacttcc | tcttacctat | gtcccttctc | atgcctttcc | ctccaacggg | 1431 |
| gaaagccaac | tccatctcta | agtgctgaac | tcatccctgt | tcctcaaggc | cacctggcca | 1491 |
| ggagcttctc | tgatgtgata | tccactttt | ttttttttg | agatggagtc | tcactctgtc | 1551 |
| acccaggctg | gagtacagtg | cacgacctc | ggctcactgc | agcctccttc | tcctgggtcc | 1611 |
| aagcaattat | tgtgcctcag | cctcccgagt | agctgagact | tcaggtgcat | tccaccacac | 1671 |
| atggctaatt | tttgtatttt | tagtagaaat | ggggtttcgt | catgttggcc | aggctggtct | 1731 |
| cgaactcctg | gcctaggtga | tccacccgcc | tcgacctccc | aaagtgctgg | gattacaggc | 1791 |
| atgagccacc | atgcccagtc | gatatctcac | tttttatttt | gccatggatg | agagtcctgg | 1851 |
| gtgtgaggaa | cacctcccac | caggctagag | gcaactgccc | aggaaggact | gtgcttccgt | 1911 |
| cacctctaaa | tcccttgcag | atccttgata | aatgcctcat | gaagaccaat | ctcttgaatc | 1971 |
| ccatatctac | ccagaattaa | ctccattcca | gtctctgcat | gtaatcagtt | ttatccacag | 2031 |
| aaacattttc | attttaggaa | atccctggtt | taagtatcaa | tccttgttca | gctggacaat | 2091 |
| atgaatcttt | tccactgaag | ttagggatga | ctgtgatttt | cagaacacgt | ccagaatttt | 2151 |
| tcatcaagaa | ggtagcttga | gcctgaaatg | caaaacccat | ggaggaattc | tgaagccatt | 2211 |
| gtctccttga | gtaccaacag | ggtcagggaa | gactgggcct | cctgaattta | ttattgttct | 2271 |
| ttaagaatta | caggttgagg | tagttgatgg | tggtaaacat | tctctcagga | gacaataact | 2331 |
| ccagtgatgt | ttttcaaaga | ttttagcaaa | aacagagtaa | atagcattct | ctatcaatat | 2391 |

```
ataaatttaa aaaactatct ttttgcttac agttttaaat tctgaacaat ttctcttata    2451
tgtgtattgc taatcattaa ggtattattt tttccacata taaagctttg tcttttttgtt   2511 gttgttgttg tttttaagat ggagtttccc tctgttgcca ggctagagtg cagtggcatg    2571
atctcggctt actgcaacct tgcctccca ggtttaagcg attcttctgc ctcagcctcc     2631
cgagtagctg ggaccacagg tgcctaccac catgccaggc taattttgt attttagta     2691 aagacagggt ttcaccatat tggccaggct ggtctcgaac tcctgacctt gtgatctgcc    2751
cgcctccatt gtgttgttat ttgtgagaaa gatagatatg aggtttagag agggatgaag    2811
aggtgagagt aagccttgtg ttagtcagaa ctctgtgttg tgaatgtcat tcacaacaga    2871
aaacccaaaa tattatgcaa actactgtaa gcaagaaaaa taaggaaaaa atggaaacat    2931
ttattccttt gcataataga aattaccaga gttgttctgt ctttagataa ggtttgaacc    2991
aaagctcaaa acaatcaaga ccctttttctg tatgtccttc tgttctgcct tccgcagtgt   3051
aggctttacc ctcaggtgct acacagtata gttctagggt ttccctcccg atatcaaaaa    3111
gactgtggcc tgcccagctc tcgtatcccc aagccacacc atctggctaa atggacatca    3171
tgttttctgg tgatgcccaa agaggagaga ggaagctctc tttcccagat gccccagcaa    3231
gtgtaacctt gcatctcatt gctctggctg agttgtgtgc ctgttctga ccaatcactg     3291 agtcaggagg atgaaatatt catattgact taattgcagc ttaagttagg ggtatgtaga    3351
ggtattttcc ctaaagcaaa attgggacac tgttatcaga aataggagag tggatgatag    3411
atgcaaaata tacctgtcc acaacaaact cttaatgctg tgtttgagct ttcatgagtt     3471
tcccagagag acatagctgg aaaattccta ttgattttct ctaaaatttc aacaagtagc    3531
taaagtctgg ctatgctcac agtctcacat ctggtgggg tgggctcctt acagaacacg     3591
ctttcacagt taccctaaac tctctggggc agggttattc ctttgtggaa ccagaggcac    3651
agagacagtc aactgaggcc aacagaggc ctgagagaaa ctgaggtcaa gatttcagga    3711
ttaatggtcc tgtgatgctt tgaagtacaa ttgtggattt gtccaattct ctttagttct    3771
gtcagctttt gcttcatata ttttagcgct ctattattag atatatacat gtttagtatt    3831
atgtcttatt ggtgcattta ctctcttatc attatgtaat gtccttcttt atctgtgata    3891
attttctgtg ttctgaagtc tacttttgtct aaaaataaca tacgcactca acttcctttt   3951
ctttcttcct tcctttctt cttccttcct ttctttctct ctctctcttt ccttccttcc     4011
ttcctccttt tctctctctc tctctctctc tctcttttct tgacagactc tcgttctgtg    4071
gccctggctg gagttcagtg gtgtgatctt ggctcactgc tacctctacc atgagcaatt    4131
ctcctgcctc agcctcccaa gtagctggaa ctacaggctc atgccactgc gcccagctaa    4191
tttttgtatt tttcgtagag acggggtttc accacattcg tcaggttggt ttcaaactcc    4251
tgactttgtg atccacccgc ctcggcctcc caaagtgctg ggattacagg catgagccat    4311
cacacctggt caactttctt ttgattagtg tttttgtggt atatcttttt ccatcatgtt    4371
actttaaata tatctatatt attgtattta aaatgtgttt cttacagact gcatgtagtt    4431
gggtataatt tttatccagt ctaaaaatat ctgtctttta attggtgttt agacaattta    4491
tatttaataa aatggtggaa tttaaa                                         4517

<210> SEQ ID NO 6
<211> LENGTH: 244
<212> TYPE: PRT
<213> ORGANISM: Homo sapiens
```

```
<400> SEQUENCE: 6

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Gln Asn His Tyr Asp
130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
            195                 200                 205

Asp Gln Val Trp Leu Gln Val Tyr Gly Glu Gly Glu Arg Asn Gly Leu
        210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 7
<211> LENGTH: 20966
<212> TYPE: DNA
<213> ORGANISM: Homo sapiens
<220> FEATURE:
<221> NAME/KEY: misc_feature
<222> LOCATION: 1..4811
<223> OTHER INFORMATION: 5' regulatory region
<220> FEATURE:
<221> NAME/KEY: exon
<222> LOCATION: 4812..4851
<223> OTHER INFORMATION: exon 1
<220> FEATURE:
<221> NAME/KEY: exon
<222> LOCATION: 15144..15365
<223> OTHER INFORMATION: exon 2
<220> FEATURE:
<221> NAME/KEY: exon
<222> LOCATION: 16277..20559
<223> OTHER INFORMATION: exon 3
<220> FEATURE:
<221> NAME/KEY: misc_feature
<222> LOCATION: 20560..20966
<223> OTHER INFORMATION: 3' regulatory region
<220> FEATURE:
<221> NAME/KEY: allele
<222> LOCATION: 3787
<223> OTHER INFORMATION: 9-27-261 : polymorphic base G or C
<220> FEATURE:
```

-continued

```
<221> NAME/KEY: allele
<222> LOCATION: 11118
<223> OTHER INFORMATION: 99-14387-129 : polymorphic base A or C
<220> FEATURE:
<221> NAME/KEY: allele
<222> LOCATION: 15120
<223> OTHER INFORMATION: 9-12-48 : polymorphic base C or T
<220> FEATURE:
<221> NAME/KEY: allele
<222> LOCATION: 15196
<223> OTHER INFORMATION: 9-12-124 : polymorphic base G or T
<220> FEATURE:
<221> NAME/KEY: allele
<222> LOCATION: 15427
<223> OTHER INFORMATION: 9-12-355 : polymorphic base G or T
<220> FEATURE:
<221> NAME/KEY: allele
<222> LOCATION: 15500
<223> OTHER INFORMATION: 9-12-428 : polymorphic base A or G
<220> FEATURE:
<221> NAME/KEY: allele
<222> LOCATION: 15863
<223> OTHER INFORMATION: 99-14405-105 : polymorphic base A or G
<220> FEATURE:
<221> NAME/KEY: allele
<222> LOCATION: 17170
<223> OTHER INFORMATION: 9-16-189 : polymorphic base deletion of A
<220> FEATURE:
<221> NAME/KEY: primer_bind
<222> LOCATION: 3528..3545
<223> OTHER INFORMATION: 9-27.pu
<220> FEATURE:
<221> NAME/KEY: primer_bind
<222> LOCATION: 3928..3946
<223> OTHER INFORMATION: 9-27.rp complement
<220> FEATURE:
<221> NAME/KEY: primer_bind
<222> LOCATION: 10990..11008
<223> OTHER INFORMATION: 99-14387.pu
<220> FEATURE:
<221> NAME/KEY: primer_bind
<222> LOCATION: 11423..11442
<223> OTHER INFORMATION: 99-14387.rp complement
<220> FEATURE:
<221> NAME/KEY: primer_bind
<222> LOCATION: 15073..15092
<223> OTHER INFORMATION: 9-12.pu
<220> FEATURE:
<221> NAME/KEY: primer_bind
<222> LOCATION: 15503..15520
<223> OTHER INFORMATION: 9-12.rp complement
<220> FEATURE:
<221> NAME/KEY: primer_bind
<222> LOCATION: 15759..15776
<223> OTHER INFORMATION: 99-14405.pu
<220> FEATURE:
<221> NAME/KEY: primer_bind
<222> LOCATION: 16191..16211
<223> OTHER INFORMATION: 99-14405.rp complement
<220> FEATURE:
<221> NAME/KEY: primer_bind
<222> LOCATION: 16982..17001
<223> OTHER INFORMATION: 9-16.pu
<220> FEATURE:
<221> NAME/KEY: primer_bind
<222> LOCATION: 17384..17402
<223> OTHER INFORMATION: 9-16.rp complement
<220> FEATURE:
<221> NAME/KEY: misc_binding
<222> LOCATION: 3775..3799
<223> OTHER INFORMATION: 9-27-261.probe
<220> FEATURE:
<221> NAME/KEY: misc_binding
<222> LOCATION: 11106..11130
<223> OTHER INFORMATION: 99-14387-129.probe
<220> FEATURE:
<221> NAME/KEY: misc_binding
<222> LOCATION: 15108..15132
<223> OTHER INFORMATION: 9-12-48.probe
```

```
<220> FEATURE:
<221> NAME/KEY: misc_binding
<222> LOCATION: 15184..15208
<223> OTHER INFORMATION: 9-12-124.probe
<220> FEATURE:
<221> NAME/KEY: misc_binding
<222> LOCATION: 15415..15439
<223> OTHER INFORMATION: 9-12-355.probe
<220> FEATURE:
<221> NAME/KEY: misc_binding
<222> LOCATION: 15488..15512
<223> OTHER INFORMATION: 9-12-428.probe
<220> FEATURE:
<221> NAME/KEY: misc_binding
<222> LOCATION: 15851..15875
<223> OTHER INFORMATION: 99-14405-105.probe
<220> FEATURE:
<221> NAME/KEY: misc_binding
<222> LOCATION: 17158..17182
<223> OTHER INFORMATION: 9-16-189.probe
<220> FEATURE:
<221> NAME/KEY: primer_bind
<222> LOCATION: 3768..3786
<223> OTHER INFORMATION: 9-27-261.mis
<220> FEATURE:
<221> NAME/KEY: primer_bind
<222> LOCATION: 3788..3806
<223> OTHER INFORMATION: 9-27-261.mis complement
<220> FEATURE:
<221> NAME/KEY: primer_bind
<222> LOCATION: 11099..11117
<223> OTHER INFORMATION: 99-14387-129.mis
<220> FEATURE:
<221> NAME/KEY: primer_bind
<222> LOCATION: 11119..11137
<223> OTHER INFORMATION: 99-14387-129.mis complement
<220> FEATURE:
<221> NAME/KEY: primer_bind
<222> LOCATION: 15101..15119
<223> OTHER INFORMATION: 9-12-48.mis
<220> FEATURE:
<221> NAME/KEY: primer_bind
<222> LOCATION: 15121..15139
<223> OTHER INFORMATION: 9-12-48.mis complement
<220> FEATURE:
<221> NAME/KEY: primer_bind
<222> LOCATION: 15177..15195
<223> OTHER INFORMATION: 9-12-124.mis
<220> FEATURE:
<221> NAME/KEY: primer_bind
<222> LOCATION: 15197..15215
<223> OTHER INFORMATION: 9-12-124.mis complement
<220> FEATURE:
<221> NAME/KEY: primer_bind
<222> LOCATION: 15408..15426
<223> OTHER INFORMATION: 9-12-355.mis
<220> FEATURE:
<221> NAME/KEY: primer_bind
<222> LOCATION: 15428..15446
<223> OTHER INFORMATION: 9-12-355.mis complement
<220> FEATURE:
<221> NAME/KEY: primer_bind
<222> LOCATION: 15481..15499
<223> OTHER INFORMATION: 9-12-428.mis
<220> FEATURE:
<221> NAME/KEY: primer_bind
<222> LOCATION: 15501..15519
<223> OTHER INFORMATION: 9-12-428.mis complement
<220> FEATURE:
<221> NAME/KEY: primer_bind
<222> LOCATION: 15844..15862
<223> OTHER INFORMATION: 99-14405-105.mis
<220> FEATURE:
<221> NAME/KEY: primer_bind
<222> LOCATION: 15864..15882
<223> OTHER INFORMATION: 99-14405-105.mis complement
<220> FEATURE:
<221> NAME/KEY: primer_bind
<222> LOCATION: 17151..17169
```

<223> OTHER INFORMATION: 9-16-189.mis
<220> FEATURE:
<221> NAME/KEY: primer_bind
<222> LOCATION: 17171..17189
<223> OTHER INFORMATION: 9-16-189.mis complement

<400> SEQUENCE: 7

```
gctgatctgc tgcctcagcc ttcccaaagt gctgtaattt attaggcata agccactgtg      60
cctgcctagt gttgtacatt ctgtgggttt tgacaattgt atgcatctac atgtatgtac     120
catttatagt attcctgttt ttaattttag ccattctagt aggcatgtag tgatatctca     180
tggtgatttt aatttgcgtt tccgtaatgg ttaataatgc tgaacatctt tgcatgtgct     240
tgtttgtcat ttgtgtttcc tacttggtga ataattgtt catgtccttt gtccattttc      300
taattgaatt ttttttttacc atttagtttt gagatttctt tatacaatct agatccaaat    360
ctcttgtctc aaatatggtt tgcaaataca ttcctctaat tcatatattg ccttttcctc     420
ctcttaacag gatgtttcac agagcaaaag ttttagtttt gttgaaatct cactttcat      480
tttttctttt agtggattgt gcttttgttg tcatatgtaa gaactcttca ctggccctag     540
atccttgtat tggtttccta agattgccat agcaaatcac catgaactta gtgacaaaaa     600
gacagaaatt tattttcact tcctactgtg ggcagactag acgttaatta ttttcatgta     660
tgctcattcc tatgacatct ttctgatata ataattatag ttattcttaa gcttcaccct     720
tttttctatt agctttgtta ccttgggtgt cacttttttct tttttgacat tgtgacctat    780
gccagatcat gtctgttagt acttagcccct ccattcacct ctccataatc ccttttgtat    840
tcctggagct tgatgcctga aatgacacat cctacattcc tttgccagat gggtaccagt    900
tagcttgtgc acatgggaga caaccgtgaa aagactgaag tggggaagaa gggaggagct     960
gttgtgtttc agtgagcgcc cttggcagtg gcggtgacag tggctcctgt tcagtggcaa    1020
tggtggagca gctagcaaga catgcagtaa gcgcaggctc ataggctatg gtccaggagc    1080
agtcaccgat tcctggtctt taggcaatat catctccctt tgcttctcca gccttctaa    1140
aattattgta ccttgactag tacaattttt tagtattggg ggtagtccaa ggacacaggc    1200
tttaaaaagt atgaattcag ggttgcctac ctgcattgac tgcgcttgaa tcatgatggc    1260
cttctggtcg gtggcaggag gtgacagtcc aaatcatgca gtagcaaacc agatacttaa    1320
attatcatct gagatacttc agaagtacag ccgtagccat accttcagaa gagataaaga    1380
aatgttctcc tggccaggcg cggtggctca cgcctgtcat tccagcactt tgggaggccg    1440
agggggtgga tcacctgagg tcgggagttc gagaccagcc tgaccaacat ggggaaaccc    1500
tgtctctact aaaaatacaa aattagcggg gcgtggtggc acatgcccat aatcccagct    1560
actcgggagg ctaaggcagg ataatcgctt gaacctgaga ggcagaggtt gcggtgaact    1620
gagatcatgc catagtactc cagcctgggc aacaagagtg aaactccatc tcaaaaaaaa    1680
aaaaagaaa aaaagataaa gaaatgttct cctttcttgc catttctagg ggtttgggga    1740
tggcgtacat tgctgcaggg cgtgctcact ctaccatctt gctccaatct ttattttca    1800
aaatacagtg cttatgcttg gttacttcag ttaagattat ttttaaaaat cataattaag    1860
caaaaatata tggccatgct taaacatatt taagataaat taagtgattt ggcctgtttc    1920
agtatcccaa ctcacatgct aacagggct tgacctgtag ctacggtacc ctggaggaaa    1980
tgatcgcatt tatttggtta tttcggtcta agtagtaata gttctgtcct gggaaaaaga    2040
ctagcctcaa ggcatttctg attgaatgtt tttcaattac agtcttttaaa ccagtatgcc    2100
acagaactgg ctcttttccac atgacggcct ttgtggtggg tggcagattg ccctgaggcc    2160
```

```
tcgcaaaatg ctaggctttc acaatgtcac tgactgacag ccaggcccag cacagtcttg    2220
gtgtgattgt ggggctaaag ttattccacc ttgtgcaata gctacagcct tctctaacca    2280
gctgcattct tataaagtta gaagaaaata cttttttttt tttgagatgg attctcgctc    2340
tgttgcccag gctggagtgc aatggtgcga tctcggctcg ctgcaacctc cgcctcctgg    2400
gttcaaacga ttctcctccc tcagacccc gagtagctgg gattgcaggt gcctgccacc    2460
acgcccggct aactttttg tatttttagt ggagacgggg tttcaccatc ttcgtcaggc    2520
tggtctcaga ctcctgacct caagtgatct gcccgcctca gcctcccaaa atgctgggat    2580
tacaggcatg agctactgtg cccggccaaa gaaaatactt tttatgccag ccctgaaact    2640
accctgaagc acatacatca accttgaggc ctcacactcc atcaagaggg gtgaagggca    2700
tgaggaatta gaaagcatag ggattttag ttagacagat ctggttcaaa tcctagactt    2760
gtgccttgaa caaattattt accctcattg aactctagat tcattatttg taaaatgaaa    2820
gacaataata gttatctcca aggaaagtt gaatatgatc attcatttat tcattaattc    2880
aacatttatt attgcctact ttgtgccagg ttctattcta ggaactaagg gatacaactt    2940
tgaataggca aaatctctgc tctcctgaag tttactttt tttttttttt ttgagacaga    3000
gtttcactct tgtcacccag gctggagcgc aatggtgctc ttggctcact gcaacctcca    3060
cctcctgggt tcaagtgatt ctcttgtctc agcctcccaa gtagctggga ctacaggtat    3120
gtgccaccac gcccggctat ttctgcattt ttagtagaga tggggtttca ccatgttggc    3180
cagactggtc tcaaactcct gatctcaggt gatatgcctg tcttggcctt ccaaagtact    3240
gggattacag gcctgagcca ctgcacctga cctgaagttt atgttctatt aaatagcaac    3300
agacagtaac ataaaccaaa aataaatagg aaaacaccat aacaaaaatc aaacagtgat    3360
ataattgaga gttgcttcta tttcttttg ttgtcttctt ggttcaatca gcctgctaaa    3420
ctatatggaa cctcatttc atgggccact tatttaagcc gggggacctt ggaaagtctc    3480
tcatgtctct catctcaacg gcctaatgtg acttctcttg aaatatttgg acattagcag    3540
gaagctgagg ctttacatca gatctttact ttaatggtgg acttgacttt actggtagat    3600
ttttaggctc tgtgtggact gtggagatga tatctgggg gcaggcagac acttgccctg    3660
cctctgtctg agaaaattct gttttggatg tcttgttgaa gttggtgctg gcatcctaag    3720
cccttgctgg ggtcgtaatt taattcatca gaatgtgtgg cttgcaagaa ccggctcaga    3780
tcctgcgctt caaaaacaaa acatgagcgt gccaagaaag tccaaggtgt tgaatgttgc    3840
cacttcaagc ctaaactttc taggaacacc taagtgggtg gcagcttcca gttctccagg    3900
ctgcttctag gccagagctg ggttccacaa gagacagaat aggcatatat atgcttaagg    3960
aactggaaaa acaggctctc tctctctcac aaacacacac acacacatac caaggtagct    4020
gtcaaaatgt tatccgaaat tttgaaacca aaaaatcttg aaagatggta ttccaatatc    4080 acatttatg taagttttct attatattag attcaaatta cgattcgagg ccacaagctt    4140
taagaattca gggccttttt aacttgccaa gccccacacc actccaggaa cttccccaca    4200
ccccagttct cagaattcat gtgcaaggtc tttcctaaat ccagggtcca ggtcagagag    4260
tggaggatgt gctctatttc ttacctgatt gcagacccct ctgacagtgc tcccttctga    4320
agcactcact gtctgaacgt acacagtctc agacttaatc atgcacagtg agcaagactg    4380
tggtgtgata attggcgtcc ctgacttatt agggcaaatc tatgggaggg ggagacctcc    4440
tggaccactg agcaattaat tcatttacat taggaagttt ctccgtcaga tgcaggaaaa    4500
```

```
aaatcttgtt ttcctgctgt ggttttgact tttgccccat cttctgttgc tgttgtagga    4560
ggcaaaataa gggtcaaggc ctggaaacac aagtgctttg actgaagctc cacttggctt    4620
ccgaagccca agctgggttg taccaggttc cctagggtgc aggctgtggg caactgccag    4680
ggacatgtgc ctgcccaccg gcctctggcc ctcactgagt tggccaatgg gaaatgacaa    4740
ttgtgaggtg gggactgcct gccccgtga gtaccaggct gttgaggctg ggccatctcc     4800
tcctcacttc cattctgact gcagtctgtg gttctgattc cataccagag ggtaagagca    4860
attctgtgaa gttccaggct gggtggggga tgcatgcata gcctctggct gggatcaccc    4920
aggctctccc gtccgtagta gtgtgggagt ggatacaggt ggatactctg gtcagagcag    4980
cactggtgga ggcagatatg cactgggctt cttcctccgt tctcccacag ccccaagaga    5040
gaaagggtta tttcagacat tccttctaag atgcatggaa ccattctgaa ttttacccag    5100
ttcgctctgt agcaggatac ctattgagaa aaagttaggg tcagtaaggt ggaagggtct    5160
gtccacagat gaagtccaat tcgattaagg gggataaggg aatacattgt ctcttagctt    5220
gaccaggtag ggcaaaggaa gaagcatata tgaaggcagc ttcagaaaag tcaagctgag    5280
cactgacttc agactggaat taggaatcca gctctgccac tttattctac tcagcaaata    5340
tttactgagc aaattctatg ggctagacag tggattgggt tcacaagata caatgagtgt    5400
gacatggttg ttgtctatgg atttggggat atatgtaggt atagggatat cttacaaggt    5460
aatcaagagg ttctaatgag gccagccatg gtggctcaca cctgtaatcc cagcaatttg    5520
ggagaccgag gcgggtggat cacctgaggt caggagttcc agactagcct gaccaacatg    5580
gtgaaacccc gcctctacca aaaatacaaa aattagttgg gcgtgatggc aggtgcctgt    5640
aatcccagct ctcgggagg ctgaggcagg agaattgtct gaacctggga ggcagaggtt     5700
gcagtgagcc gagattgttg ccactgcatt ccagcctggg tgacagagcg actttgtg     5760 tcaaaaaaaa aaaaaaaag aaagaaaaga aaagaggct ctaatgagat aaaatgagaa       5820
aagcctggca tgtagtggca acttatgaaa aattgtaatt aaaaaaaaac attttctgac    5880
agaagaaact ggatctacct ggtttttctg aagcctaatc ctgctcgccc cagtgagtgc    5940
tgtttctgag gcatcctggt tgtttttgagc tgtggatgct gaaggttaga gtgggaggga   6000
ttttagaggt taggtctgcc cctcttgtgt tagaggacat ggatccctgg tctggagagg    6060
ttctggtttt tggatcaagc ctcacaaggg gtggcaccaa ctcactccta ggaactccgc    6120
tagaaggaag gccagctctg cctaattcgg ttggggagat gggggtccct ttatgctagc    6180
agaatatgtc cgaaggagca tgatggtgtc agctttgttc atgaaggcca gtggtacaca    6240
gggagcccgg cagcttcctc agcagtccct gctgccactc ttccttaagt cttgaggagt    6300 cttttttttgg cacaatctca gctcactgca acctccgcct cccaggttca agcgattctc    6360
ctgcctcagt ctcccaagta gctgagacta caggcatgcg ccaccacgcc cagctaattt    6420 ttatatttt agtagagatg gggttcacca tattggccag gatggtctcg atctcttgac      6480
ctcatattcc acctgcctcg gcctcccaaa gtgctggtat tacaggtgtg agccactgcg     6540
cctggccgag gagtcttaag ctgagatcac agcattgcac tccagcctgg gcaaaaagag   6600
caaaactcca tctcaaaaaa aaaaaaaaaa tagacacaag actggctcct tgtcttttt     6660 ggggacaggg tctcactcta tcacccaggc tggagtgcag tggtgcaatc acagctcact    6720
gcagcctcga tttcccaggc tcaagtgacc ctcccatctt agcctcctga gtagctggga    6780
ctacaggtgt gtgcaaccat gcctggctaa ttttttaaaaa ttttttgtag agatgaggtc   6840
tcactatatt ggctgggggg cctcaaactc ctgggctcag cagtcctccc acctcagcct    6900
```

```
cccaaaaggc tgggattata tgcttgctct ttttaaggtg gctgtaggga caaactttcc    6960
acctactcct tgtcaagcca gtggaccggt ggtcccagac atacggctaa agtcaagagg    7020
tgatgtcttt tggagagata ctttcaatca ggaatttcaa tcagaaattc aatcatgtgg    7080
agagagactt atcctaaaaa tgtggtggtg cgtgggatgc tctgttttat tagttccttg    7140
acagtatgta tgtgtgtgag tgtgtgtgtg tgcgcgcgca cactcatttg gatgggtgtg    7200
tatgtgtgtg ggggggtggt gcgtacgtat gtggatgtgt ggatgtggtg tgtgggtgtg    7260
cgcgtgcata ggtggaggtg tgtgtatggg tgcgggtatg tgtgtgtgtt gggcatggag    7320
atattgacag ctctcccagg gctgagtgaa ggctttcggg caaagctcct gggagctagg    7380
caaagctgag ttgattcctg ttatgccat ttattattgg gttgcaccgt gtgaaactgc     7440
caatattcta cactttgact tttatttatt tttatttta ttttttttga gacagagttt     7500
cacacttgtc acctaggctg gagtgcagtg gcgcgatctc agctcactgc aacctctgcc    7560
tcatggattc aagtgattct cctgcctcag cctcccaagt agctggaatt acaggtgccc    7620
gctaccacgc ctgactaatt tttgtatttt tggtagagac gggatttcac catgttgtcc    7680
aggctggtct gaaactcctg acatcaggta atccacccac ctcagcctcc caaagtgctg    7740
ggattacagg catgagccac tgcgcccggc ccattttgac ttttaaaaat gggagtttga    7800
tataattcaa tccagtggtt gaattagcta gcatcgttcc ctctccaagt ctcaggttct    7860
cctacacgtt agagtcaaaa gcagggctat gggaagatta agtaaaataa attttgaaaa    7920
tgccttatga aaattacact ccaaagaact cgcgccagtg tcagtgttct catgttcctc    7980
atctcacatg atcacatttc gcggattagg aagctgagtc tgagaagctc cgtgtagtgc    8040
tttttcggag gcaccgtgat gtgatggaag gctcactcgt taggaagtca gaacagagtc    8100
tctgagggat catttcctta atctgtcagt ttcctcatct ctgaagttgg gctcatttcc    8160
ttccttcatg gagttattgt aaagatgaag ataaataacg tgtaaaatct agcatgggaa    8220
ctggcttcta taaggttcta ataagtgcat tcctactcct tcccctcagc cttcccattt    8280
gtaaaagcaa gcaggggtg aggtgatttc tggggctcct tttggctctg acatttgagg     8340
attttgtatc cttttttttt tcagagtctt gctctgtcac ccaggttgga gtgcagctca    8400
atgcaaattc cgcctcccag gctcaagcaa ttccttatgtc tcagcctcct gagtacctgg    8460
gattacaggc aggcaccacc acccccagct aatttttgt attttcagta gagacggggt      8520
tttgccatat tggccaggct ggtcttgaac tcctgacttc atgtgaccca cccatctcag    8580
cctcccaaag tgctgagatg acaggtgtga gctaccgtgc ctggccaatt ttgtgtgctt    8640
taatgccctt ttctgctgga agagttggca ccaggtttgg tgatctcttt ccccacacg     8700 gctctgcctc ctgccagtcc cagaggggac cctgtccttg catttcacag gattctgctg    8760
ttgcaactga aattccagta ggtcaaagtg aaatttctca tacactttaa catgaagata    8820
aatgatcaca gtatggccct ttaggatcct gagaacatca cggtcatccc ctggtataat    8880
tttaaaagca gatgaatcca tgcctgtgcg aggtttgcca ggaaagccag tgctgggatt    8940
acagtggaag tctttttatg ctactttttt cttgtatccc tcaccccatg gggtggcata    9000
ttgaaaggca ggatgtgtga ccacgatact tttctcctcc tggactatgt ctaagagtct    9060
gttattgggt tctgaagatc agagtttaat ttccgactcc tctctgtgta gctctgggat    9120
cttggaaagc cacttaacct ttctgaagtc ccctttcctc atctctaaaa tgcatacact    9180
catcactaac atttactgag cactgacatg tgccagacac cattctaagc attttacaca    9240
```

```
gactacacca tttgatcttc caacaaacag aacactgaaa cgcattacag gtcagaacaa   9300
atgatttgtg cctaagcacc aagaccgtag agcccgtgct ccctattcta ccctatcctg   9360
tctctcaaaa tgattgtgag aatcgaatga gacactaggt gagaaaaggg ttttataaat   9420
agcattttaa aaattttta aagtccacaa aattttaat tttaatacag ataaaataga    9480
tccctttgtt ttataaaaag taacaaaatt tgttatacaa caactatgtt atttattaat   9540
tttgccttt tgtatgctgc caggaaagaa acattaagaa atcttaaatt gattatggtg    9600
aatcagaagg tctgcctgga ctttttattg ctctaactgt acagctgatc atactacctc   9660
attttttttt atgacacttc aagggtgcgc ttagcttcat cactccttcg ttgccaaaag   9720
ctttgtgacc aaaaacaatt aagcagattc ctgagtcact aaatgacaca taaccagagt   9780
tgagacttag gaacttttag tgccatgcta agcccacagg gacacaacaa atagcatttt   9840
acaaaggcaa agaattgtga cacttgagat ttagcttgtt gatccttgta aaagtttct    9900
ttttaggcat aattgagttt tagatcatag tactcactat tacttagtaa taatttttt    9960
ctgatagaaa tacagtgtaa caggccgggc gcagtggctc atgcctgtaa tcccagcact  10020
tgggaggcc gaggcgggcg gatcacttga ggtcaggagt ttgagaccag cccggccaac   10080
atggtgaaat cccatctcta ctaaaaatac aaaaaattag ccaggtgtgg tcgtggattc  10140
ctgtgatccc agctacttgg gagggtgagg caggagcatc agttgaaccc aggaggcgga  10200
ggttgcagtg agccaagatg gtgccattgc actccagcct gggccacaaa gcgagactcc  10260
acttcagaaa caaaaaaaaa aagagagaga gagaaaagaa ggaaggaagg aaggaaggaa  10320
ggaaagaagg aaggaaggaa ggaaagaagg aaggaaggaa ggaaggaaag aaggaaggaa  10380
ggaaagaagg aaggaaggaa agaaggaagg aaggaaggaa ggaagggtaa caagcaaagt  10440
gtaacaatgg caatatctaa aaaaataggt attttatat gtttgtcgtt ttatatatat   10500
gacccccact ttagagatga ggaaactgag agattaagga aacgatccct gagagactct  10560
gttctgactt ccaaatcggt gagctttcca tcgcatcacg gtgcctccga aagcatgaca  10620
cggagcttct cagacttagc ttcctaatcc gctaaacggg attatgtgag atgaggaaca  10680
tgagaacgct gacatgggtg agggttcctt ggagtatcat tttcatgtgg cattttcaaa  10740
acttatttta cctaatcttc ccaaagcct gcttttgact ctaatgtgtc tcctgagact   10800
tggagagcgc aagatgctag cgacagagca agactccatc tccagataaa taaataagta  10860
aaataaaaaa gaacacaaat aattttgaaa attttttga aaattaggca cgtttgcact   10920
gaccttcaat tgttattaat tgctggtttc ccacccagaa ttaagttgga atgcaacttt  10980
cttttacaat cagagtccgt tcttggtctt ggaaacttct gaggctcctg tgctaatccc  11040
actcttgtat ttttggcacc tctaccccgt gccactgtca tggaacccag gctgatcgca  11100
cctattagtg gagaaatmtg tccataaatac tgaagtttgg ggacaaacag tgttcccta   11160
gggtaggaga aagagatctt tattttaac aaagggggag gagccagaaa actccagaga   11220
cccctgagtt tgccctctct ccaaggtttg gggtaagccc ccgtcaccc tttatctctg    11280
gggctttcac atattctgga ttctctcctc ctgtttccca gcagaaaagg atggagcctc  11340
acagattctt cccatttctg gagaaaaaca tgcatggagc tcaaagttct tctcaggagt  11400
tttattgcca aagccataat aagaaagggt ggaggtgaca agcagtgagg aagtttaaag  11460
atgcatgaaa tctgtaaagt ctcagaacaa gaattctcct aaaatgcaaa aggggctttg  11520
ctggtctccc cttggcttct catgtagctc acctcttttt tcttatcttg agactagtca  11580
aacctaagct gtttctcatt ttatttccag aagctattga gaacactctc ctgaattctt  11640
```

```
caaattcagt agagggcgac aaatgtacat ataaatgatg gtagtgggtc ttaaataaag    11700
actcatgaca cctaaagggg cagcacctga gtctgattgc acctgtttct gttgctgttt    11760
ctgtctctct tctctctgtc tgccatttca ttatcaatgg ttactttact tataagatca    11820
tattagaacc tgatatttga taaatgatgc atcagatcta tagtgagaga aaaaattaat    11880
gcaattaaag gtgttgtaac agctagtctt caagtgggga gaaatcattt gagtacctta    11940
ggtcacagct tacatcaaaa caaaaaatca gagctacatt aaaaagtgaa attttaacta    12000
tatcaaacaa tagaaaaaaa cagaagaaaa ttgaatactt actaaatctt agcatgaata    12060
agaactgttt aacacttaga ggcaaggact gggcgtggtg gctcatgctt ttaatcccag    12120
gactttggga gcccaaggcg ggcggatcac ctgaggtcag gagtttgaga ctagcctggc    12180
caacatggtg aaaccccgtc tctactaaaa aatgcaaaaa ttagctgcgt gtggtggtgc    12240
atgcctgtaa tctcagctac ttgggaggct aaggcatgag aatcgcttga acctgggagg    12300
tggaggctgt agtgagccga gattgtgcca ctgcactaca gcctgggtga cagtgtgaaa    12360
tcctctctct caaaaaaaaa aaaaaaaaaa agcaaactag agcagtgagg taccattatt    12420
tcctttgctc actaaactga caacacacaa atgtttttta taatacccaa agctgatgag    12480
ggtagttaag gtatgccctt ttatacacac actaatgatg tactactggt tggcagtata    12540
acatatgctg ccatgtgggg atatgtatca ggagacttaa aaatgtgcat accttttggt    12600
ccagtaattt acttctggga atctgtcata acagaataat aatcttgggg aaagctacat    12660
gcctaaggat atttaaaata ttatttaaaa atcaaagtat aatttcttac agaatataaa    12720
ataatatttt aaaatgaaaa tatgctaaaa gtttgatgaa atataaatgg tcaaatatat    12780
attgattata tccacttact agactagcac tcactctgag acgttaaaaa tagtcattat    12840
aaaaactaga aaatgccaaa gacaaaataa aggaataaag ttttacataa agtatgattc    12900
cactatgttt aaaaataaac agagacattc ttggagttga gtattgtttt cttttctgtc    12960
atgtccaaag aactatataa ctattatttt taatgaacta tatatgtaat atatacatat    13020
agtttatatg tatatacaaa atttatctca tatatatgat aaagatgaaa gatgagttgg    13080
atgtgccacg tgaagtgggt agtatagaaa cccaggtaat ggggcatagg agtgggattc    13140
cagataccag gccatgtttt tgggggtgag attgccaatc acggtctttc ttccatccct    13200
cacagaggag taggtttgtc ttcaacaaac cttcagttgt cctgaagaca aacctaattc    13260
tggagacttc atataatcta gaagagacaa gcaaactgat gaaaaatagt gaattttaa    13320 ggtaaaataa agtacatgga ctacactttg tttagaatca gattcttggg attaaccaca    13380
ttaacccaca gagggtctta gtgatgcctc taatccagga tcctaggacc tatttctctc    13440
tgtgagatgc tttctcccaa ctccttggtg agagtgggaa gactaagacc tcagcaatct    13500
gaggtggagg cctaagatcc ccctaagatc ggaggcagaa tctgagaggg gataaaagtc    13560
cctatacctg tattgggccc ttttctggga gggggatatc aaagaatgat tttgagacag    13620
ggaggctttt gactacctgt gccacttgag ctctttgcta gggctccaga atacatattt    13680
caaatacatt cccccctccct ccttccttcc ctcttccact cttccttttt atcttccttt    13740
cttcttttcc ttcctccttc ccttcctttc tctggctctc tcatgatttc ttttcctcat    13800
tataaaagtg cttatttagt ccctactctg ctattagtgt gttagtcttt gtcccctggt    13860
acttgctgtt taatggagaa atgggtgagc aaaacagaaa ttcagcagaa gtgcaataat    13920
agagctaagc caggtgtata aatccattct cacactgctg taaaaaacta ctgggtaatt    13980
```

```
tataaagaaa agaggtttaa ttgactcaca gttccacagg ctgtacagga agcatggctg   14040
gggaggcctc agaaaactta caatcatggt ggaagaaaga gcgaagggga agcaagcaca   14100
tcacacagca gcaggagaga gagagagaaa gagagagaga gagaatatag gggaagtgct   14160
acacactttc aaccagatct tgtgagaatt cacctactat catgagaaca gcaagggata   14220
agtctgcctc catgattcag tcacctccta ccaggcccct tctccaacac atgtcgacgt   14280
gctatttggg tggggacaca gacccaaacc atattaccag ggcactggag aaacacagag   14340
gggaaagaac cagccaagga gtgagatgga aacaaggag gacttcttga aacagatgac    14400
atccaaactg ggtcctgaaa gctgaataga gattagacag gggaggaggg gcagctaaag   14460
atggctcagg caaacaaagg gccaggggat atgttcatgg gatgatgtgt ctctcgttgt   14520
ctgcttaaca caaggtgagt ctctccctcc ctctctctct cttttctct gtgtgtgttt     14580 gtgtgtgtgc atgtgtgcaa atgtaatata cccaatagtc aaacatgtgc cccaggagag   14640
gggtagagga agaaagagaa tgagagagta agaaggagga atagacacag aaaatgagag   14700
agaagggggg aaagaaaaag aagaaggag ccagaggaga gaagctggtt agcattgaat    14760
ggagcaatct gtgtcatcgt acttgggaaa cccaaggatg gattcttggc aagtcgactc   14820
ttggagcttt ccctgtgctt ggtcctgtgc tcagacatgg gaaaattaga ggagtgtcat   14880
ctgtgcaatc actgaattca taatcttggt gaggaaagga gactacacac agggaataat   14940
gctaagtatt acagatttca gggcagaaag agatcaaggt gggctgcaat attcagaaaa   15000
gtcttcctgg aaaagttgaa tacttagaaa gcagctccta gaagtagact ctgctgagat   15060
ggacggagtc ctttgtaggt cccaactggg tgtgtgtgtg gggtctgtct ctccatggcy   15120
gacagtgcac atgtggattc cagggctcag gatgctgttg ctgggagctg ttctactgct   15180
attagctctg cccggkcatg accaggaaac cacgactcaa gggcccggag tcctgcttcc   15240
cctgcccaag ggggcctgca caggttggat ggcgggcatc ccagggcatc cgggccataa   15300
tggggcccca ggccgtgatg gcagagatgg caccccctggt gagaagggtg agaaaggaga   15360
tccaggtaag aatgtttctg gcctctttca tcacagacct cctacactga tataaactat   15420
atgaagkcat tcattattaa ctaaggccta gacacaggga gaaagcaaag cttttttatg   15480
ttaaccataa gcaacctgar gtgatttggg gttggtcttc caaggatgag tgtagatggt   15540
gcctctataa ccaagacttt ggctttgctg catctgcagc tccttttcca tccccttcc     15600 catcttcacc ctcatcccta ttcccagtac attcatattc tgattcctct ttctgtctgc   15660
ttaacttcca tttcacccag tggcattcaa ccacatttac tgcacacccc ctgaaaggct   15720
cagtcctgcc tttggggaac tcttgatcta ggtaagatgt ctaatgtgca aggctctgtt   15780
ggtggttacc acaagaaagt ctactctaaa aatgtcaaac tgaatgtgaa caagtattca   15840
aagtatggag catagagaaa atrtactcac cgtggacctg atgaagaatg aaggcttcaa   15900
ggaggaggca gagcttcagc taggccttga atgatgggta ggcagaatag aggaggagag   15960
acatcctaga tggaggggt agaattgcaa aaccagggtt gatggtgcca gcacataaag    16020
ggctggcagg gtgagggtc tatgatagag acctatagga gataaagata gagttgaaat    16080
tatgggagcc tccatgtctg tgggagatat agaaggagga ggtaacacct ctctcctttt   16140
gggagctctt attggtttct tgatctataa gtcaagaagg ttgtgagtgg gagccacagg   16200
gatggtaatt taggctgtaa ccaacctagg caggagttct gttctttgta gtcactgagg   16260
tcttctcatt ccttaggtct tattggtcct aaggagacca tcggtgaaac cggagtaccc   16320
ggggctgaag gtccccgagg cttttccggga atccaaggca ggaaaggaga acctggagaa   16380
```

```
ggtgcctatg tataccgctc agcattcagt gtgggattgg agacttacgt tactatcccc    16440
aacatgccca ttcgctttac caagatcttc tacaatcagc aaaaccacta tgatggctcc    16500
actggtaaat tccactgcaa cattcctggg ctgtactact ttgcctacca catcacagtc    16560
tatatgaagg atgtgaaggt cagcctcttc aagaaggaca aggctatgct cttcacctat    16620
gatcagtacc aggaaaataa tgtggaccag gcctccggct ctgtgctcct gcatctggag    16680
gtgggcgacc aagtctggct ccaggtgtat ggggaaggag agcgtaatgg actctatgct    16740
gataatgaca atgactccac cttcacaggc tttcttctct accatgacac caactgatca    16800
ccactaactc agagcctcct ccaggccaaa cagccccaaa gtcaattaaa ggctttcagt    16860
acggttagga agttgattat tatttagttg gaggccttta gatattattc attcatttac    16920
tcattcattt attcattcat tcatcaagta actttaaaaa aatcatatgc tatgttccca    16980
gtcctgggga gcttcacaaa catgaccaga taactgacta gaagaagta gttgacagtg    17040 ctattttgtg cccactgtct ctcctgatgc tcatatcaat cctataaggc acagggaaca    17100
agcattctcc tgttttaca gattgtatcc tgaggctgag agagttaagt gaatgtctaa    17160
ggtcacacaa gtattaagtg acagtgctag aaatcaaacc cagagctgtg gactttgttc    17220
actagactgt gccctttat agaggtacat gttctctttg gagtgttggt aggtgtctgt    17280
ttcccacctc acctgagagc cattgaattt gccttcctca tgaattaaaa cctcccccaa    17340
gcagagcttc ctcagagaaa gtggttctat gatgaagtcc tgtcttggaa ggactactac    17400
tcaatggccc ctgcactact ctacttcctc ttacctatgt cccttctcat gccttttcсct    17460 ccaacgggga agccaactc catctctaag tgctgaactc atccctgttc ctcaaggcca    17520
cctggccagg agcttctctg atgtgtatc cacttttttt tttttttgag atggagtctc    17580
actctgtcac ccaggctgga gtacagtgac acgacctcgg ctcactgcag cctccttctc    17640
ctgggtccaa gcaattattg tgcctcagcc tcccgagtag ctgagacttc aggtgcattc    17700
caccacacat ggctaatttt tgtattttta gtagaaatgg ggtttcgtca tgttggccag    17760
gctggtctcg aactcctggc ctaggtgatc cacccgcctc gacctcccaa agtgctggga    17820
ttacaggcat gagccaccat gcccagtcga tatctcactt tttattttgc catggatgag    17880
agtcctgggt gtgaggaaca cctcccacca ggctagaggc aactgcccag gaaggactgt    17940
gcttccgtca cctctaaatc ccttgcagat ccttgataaa tgcctcatga agaccaatct    18000
cttgaatccc gtatctaccc agaattaact ccattccagt ctctgcatgt aatcagtttt    18060
atccacagaa acattttcat tttaggaaat ccctggtttt aagtatcaat ccttgttcag    18120
ctggacaata tgaatctttt ccactgaagt tagggatgac tgtgattttc agaacacgtc    18180
cagaattttt catcaagaag gtagcttgag cctgaaatgc aaaacccatg gaggaattct    18240
gaagccattg tctccttgag taccaacagg gtcaggaag actgggcctc ctgaatttat    18300
tattgttctt taagaattac aggttgaggt agttgatggt ggtaaacatt ctctcaggag    18360
acaataactc cagtgatgtt cttcaaagat tttagcaaaa acagagtaaa tagcattctc    18420
tatcaatata taaatttaaa aaactatctt tttgcttaca gttttaaatc ctgaacaatt    18480
ctctcttaca tgtgtattgc taatcattaa ggtattattt tttccacata taaagctttg    18540 tcttttttgtt gttgttgttg tttttaagat ggagtttccc tctgttgcca ggctagagtg    18600
cagtggcatg atctcggctt actgcaacct ttgcctccca ggttcaagcg attcttctgc    18660
ctcagcctcc cgagtagctg ggaccacagg tgcctaccac catgccaggc taatttttgt    18720
```

```
atttttagta aagacagggt ttcaccatat tggccaggct ggtctcgaac tcctgacctt    18780
gtgatctgcc cacctccatt tttgttgtta tttttttgaga aagatagata tgaggtttag   18840
agagggatga agaggtgaga gtaagccttg tgttagtcag aactctgtgt tgtgaatgtc    18900
attcacaaca gaaaacccaa aatattatgc aaactactgt aagcaagaaa aataaaggaa    18960
aaatggaaac atttattcct ttgcataata gaaattacca gagttgttct gtctttagat    19020
aaggtttgaa ccaaagctca aaacaatcaa gacccttttc tgtatgtcct tctgttctgc    19080
cttccgcagt gtaggcttta ccctcaggtg ctacacagta tagttctagg gtttccctcc    19140
cgatatcaaa aagactgtgg cctgcccagc tctcgtatcc ccaagccaca ccatctggct    19200
aaatggacat catgttttct ggtgatgccc aaagaggaga gaggaagctc tctttcccag    19260 atgcccagc aagtgtaacc ttgcatctca ttgctctggc tgagttgtgt gcctgtttct     19320
gaccaatcac tgagtcagga ggatgaaata ttcatattga cttaattgca gcttaagtta    19380
ggggtatgta gaggtatttt ccctaaagca aaattgggac actgttatca gaaatagag    19440 agtggatgat agatgcaaaa taatacctgt ccacaacaaa ctcttaatgc tgtgtttgag    19500
ctttcatgag tttcccagag agacatagct ggaaaattcc tattgatttt ctctaaaatt    19560
tcaacaagta gctaaagtct ggctatgctc acagtctcac atctggttgg ggtgggctcc    19620
ttacagaaca cgcttttcaca gttaccctaa actctctggg gcagggttat cctttgtgg    19680 aaccagaggc acagagagag tcaactgagg ccaaaagagg cctgagagaa actgaggtca    19740
agatttcagg attaatggtc ctgtgatgct ttgaagtaca attgtggatt tgtccaattc    19800
tctttagttc tgtcagcttt tgcttcatat attttagcgc tctattatta gatatataca    19860
tgtttagtat tatgtcttat tggtgcattt actctcttat cattatgtaa tgtccttctt    19920
tatctgtgat aattttctgt gttctgaagt ctactttgtc taaaaataac atacgcactc    19980
aacttccttt tctttcttcc ttcctttctt tcttccttcc tttctttctc tctctctctc    20040
tttccttcct tccttcctcc ttttctttct ctctctctct ctctctcttt ttttgacaga    20100
ctctcgttct gtggccctgg ctggagttca gtggtgtgat cttggctcac tgctacctct    20160
accatgagca attctcctgc ctcagcctcc caagtagctg gaactacagg ctcatgccac    20220
tgcgcccagc taattttttgt attttttcgta gagacggggt ttcaccacat tcgtcaggtt    20280
ggtttcaaac tcctgacttt tgtgatccac cgcctcggcc tcccaaagtg ctgggattac    20340
aggcatgagc catcacacct ggtcaacttt cttttgatta gtgttttttgt ggtatatctt    20400 tttccatcat gttactttaa atatatctat attattgtat ttaaaatgtg tttcttacag    20460
actgcatgta gttgggtata atttttatcc agtctaaaaa tatctgtctt ttaattggtg    20520
tttagacaat ttatatttaa taaaattgtt gaatttaaga tggatgactg ttttatttgt    20580
ttgctgttca ccacttctgt tttattctct ttccagaatt cttttggatt gtttaaatat    20640
ttcataatat tttatcttaa tttatttatt gggtatttgc ctatatctct ttgtggtatt    20700
ttttagtggt tgcttgaggg attacaatgt acttaacttt tcacagtgtg cataaagtta    20760
atattttgcc acttgcagta aaccgtagaa ggcttataat catattagta cctctatcca    20820 cttttctttta tgttgtagtt gtcatatata ttacatctat atacactgaa acattatagg    20880
caatgttatg attttttgcat tcgtcagtca tatatatatt ttaaagaatt taagaggaga    20940
aaaatacata ttcagatatt catcat                                         20966
```